(12) United States Patent
Song et al.

(10) Patent No.: US 10,689,709 B2
(45) Date of Patent: Jun. 23, 2020

(54) KIT AND METHOD FOR DETECTING MUTATIONS IN CTNNB1 AND HTERT, AND USE THEREOF IN HCC DETECTION AND DISEASE MANAGEMENT

(71) Applicant: JBS Science Inc., Doylestown, PA (US)

(72) Inventors: Wei Song, Audubon, PA (US); Surbhi Jain, Doylestown, PA (US); Jamin Dean Steffen, Yardley, PA (US); Jeremy Wang, Collegeville, PA (US)

(73) Assignee: JBS Science Inc., Doylestown, PA (US)

( * ) Notice: Subject to any disclaimer, the term of this patent is extended or adjusted under 35 U.S.C. 154(b) by 6 days.

(21) Appl. No.: 15/492,385

(22) Filed: Apr. 20, 2017

(65) Prior Publication Data
US 2017/0369947 A1  Dec. 28, 2017

Related U.S. Application Data

(60) Provisional application No. 62/325,457, filed on Apr. 20, 2016.

(51) Int. Cl.
| C07H 21/02 | (2006.01) |
| C12P 19/34 | (2006.01) |
| C07H 21/04 | (2006.01) |
| C12Q 1/68 | (2018.01) |
| C12Q 1/6886 | (2018.01) |
| C12Q 1/6858 | (2018.01) |

(52) U.S. Cl.
CPC ......... *C12Q 1/6886* (2013.01); *C12Q 1/6858* (2013.01); *C12Q 2600/154* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 6,358,690 B1 | 3/2002 | Krysan et al. | |
| 6,664,046 B1 * | 12/2003 | Chang | C12Q 1/6886 435/6.12 |
| 6,773,882 B2 * | 8/2004 | Hogan | C12Q 1/6895 435/471 |
| 2005/0244830 A1 * | 11/2005 | Frebourg | C12Q 1/68 435/6.11 |
| 2013/0078630 A1 | 3/2013 | Bodepudi et al. | |
| 2014/0155279 A1 | 6/2014 | Song et al. | |
| 2015/0141320 A1 | 5/2015 | Krieg et al. | |
| 2015/0240299 A1 * | 8/2015 | Imanishi | C12Q 1/6858 435/6.12 |
| 2015/0315636 A1 | 11/2015 | Nadeau et al. | |
| 2016/0053253 A1 | 2/2016 | Salathia et al. | |

OTHER PUBLICATIONS

Diffenbach (PCR methods and Applications (1993) vol. 3, pp. S30-S37) (Year: 1993).*
Roux et al (PCR Methods and Applications (1995) vol. 4, pp. s185-s194) (Year: 1995).*
Le Guellec, Sophie et al., "CTNNB1 Mutation Analysis Is a Useful Tool for the Diagnosis of Desmoid Tumors: A Study of 260 Desmoid Tumors and 191 Potential Morphologic Mimics", *Modern Pathology*, Jul. 6, 2012, vol. 25, p. 1551-1558.
Reitman, Zachary J., et al., "Promoting a New Brain Tumor Mutation: TERT Promoter Mutations in CNS Tumors", *Acta Neuropatholgica*, Nov. 12, 2013, vol. 6, Issue 6, p. 789-792.
International Search Report and Written Opinion for corresponding International Application No. PCT/US2017/028668, dated Aug. 17, 2017.

* cited by examiner

*Primary Examiner* — Katherine D Salmon
(74) *Attorney, Agent, or Firm* — Pattao, LLC; Junjie Feng

(57) ABSTRACT

Provided herein are a kit and method for detecting mutations in CTNNB1 and hTERT, and their use in detection and management of hepatocellular carcinoma (HCC). The kit comprises a first pair of primers, configured to specifically bind sequences flanking the genomic region for amplifying the genomic region in a first PCR reaction; and at least one clamp, each configured to bind to one first allele but not any second allele at an annealing temperature in the first PCR reaction to thereby selectively suppress amplification of the one first allele but still allow amplification of other second allele(s). Kits and methods for detecting mutations in CTNNB1 and hTERT are also provided. A method for detecting or monitoring recurrence of HCC is further disclosed, which comprises determining levels of five DNA markers, including CTNNB1 mutations, hTERT mutations, TP53 mutations, RASSF1A methylation, and GSTP1 methylation.

3 Claims, 22 Drawing Sheets
Specification includes a Sequence Listing.

| Sample ID | qPCR detected | % Mutant Copies | Sequencing (-)BNA | Sequencing (+)BNA |
|---|---|---|---|---|
| A1K | NO | | x | |
| A2K | NO | | x | |
| A3K | NO | | x | |
| A5K | NO | | x | |
| A8K | NO | | x | |
| A9K | NO | | x | |
| A11K | NO | | x | |
| A16K | NO | | x | |
| A17K | NO | | x | |
| A18K | NO | | x | |
| A19K | NO | | x | |
| A22K | NO | | x | |
| A25K | NO | | x | |
| A26K | NO | | x | |
| A27K | NO | | x | |
| A28K | NO | | x | |
| A30K | NO | | x | |
| A31K | NO | | x | |
| A33K | NO | | x | |
| A36K | NO | | x | |
| A46K | NO | | x | |
| A47K | NO | | x | |
| A68K | NO | | x | |
| A21K | YES | 32.1 | x | x |
| A35K | YES | 33.0 | x | |
| A49K | YES | 37.2 | x | x |
| A53K | YES | 37.6 | G/A32 | G/A 32 |
| A4K | YES | 40.9 | x | x |
| A23K | YES | 41.8 | x | C/G 37 |
| A38K | YES | 158.4 | C/G 33 | C/G 33 |
| A48K | YES | 224.6 | A/T 32 | A/T 32 |
| A65K | YES | 467.5 | x | C/T 33 |
| A10K | YES | 484.0 | C/T 33 | C/T 33 |
| A64K | YES | 794.2 | x | C/T 33 |

FIG. 3B

HCC (n=84) vs. non-HCC (97 hepatitis and 106 cirrhosis)

| Specificity (%) | Sensitivity (%) | | |
|---|---|---|---|
| | AFP | Urine DNA markers | Urine DNA markers plus AFP |
| 80 | 75 | 84.5 | 94 |
| 90 | 63.1 | 84.5 | 89.3 |

Month to either recurrence(Pos) or last urine collection (Neg)

```
                               SEQUENCE LISTING

<160> NUMBER OF SEQ ID NOS: 16

<210> SEQ ID NO 1
<211> LENGTH: 18
<212> TYPE: DNA
<213> ORGANISM: Homo sapiens

<400> SEQUENCE: 1
gcagcaacag tcttacct                                                       18

<210> SEQ ID NO 2
<211> LENGTH: 40
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(24)
<223> OTHER INFORMATION: non-complementary accessory tag
<220> FEATURE:
<221> NAME/KEY: misc_feature
<222> LOCATION: (25)..(40)
<223> OTHER INFORMATION: CTNNB1 sequence

<400> SEQUENCE: 2
ctgtgtgctc ttcgtgtgtg gtgtctgtgg tagtggcacc                               40

<210> SEQ ID NO 3
<211> LENGTH: 18
<212> TYPE: DNA
<213> ORGANISM: Artificial Sequence
<220> FEATURE:
<223> OTHER INFORMATION: BNA clamp
<220> FEATURE:
<221> NAME/KEY: misc_feature
<222> LOCATION: (2)..(2)
<223> OTHER INFORMATION: bridged nucleic acid
<220> FEATURE:
<221> NAME/KEY: misc_feature
<222> LOCATION: (3)..(3)
<223> OTHER INFORMATION: bridged nucleic acid
<220> FEATURE:
<221> NAME/KEY: misc_feature
<222> LOCATION: (5)..(5)
<223> OTHER INFORMATION: bridged nucleic acid
<220> FEATURE:
<221> NAME/KEY: misc_feature
<222> LOCATION: (6)..(6)
<223> OTHER INFORMATION: bridged nucleic acid
<220> FEATURE:
<221> NAME/KEY: misc_feature
<222> LOCATION: (8)..(8)
<223> OTHER INFORMATION: bridged nucleic acid
<220> FEATURE:
<221> NAME/KEY: misc_feature
<222> LOCATION: (9)..(9)
<223> OTHER INFORMATION: bridged nucleic acid
<220> FEATURE:
<221> NAME/KEY: misc_feature
<222> LOCATION: (11)..(11)
<223> OTHER INFORMATION: bridged nucleic acid
<220> FEATURE:
<221> NAME/KEY: misc_feature
<222> LOCATION: (12)..(12)
<223> OTHER INFORMATION: bridged nucleic acid
<220> FEATURE:
<221> NAME/KEY: misc_feature
```

```
<222> LOCATION: (14)..(14)
<223> OTHER INFORMATION: bridged nucleic acid
<220> FEATURE:
<221> NAME/KEY: misc_feature
<222> LOCATION: (15)..(15)
<223> OTHER INFORMATION: bridged nucleic acid
<220> FEATURE:
<221> NAME/KEY: misc_feature
<222> LOCATION: (17)..(17)
<223> OTHER INFORMATION: bridged nucleic acid
<220> FEATURE:
<221> NAME/KEY: misc_feature
<222> LOCATION: (18)..(18)
<223> OTHER INFORMATION: phosphorylation modification

<400> SEQUENCE: 3
ggactctgga atccattc                                                 18

<210> SEQ ID NO 4
<211> LENGTH: 26
<212> TYPE: DNA
<213> ORGANISM: Artificial Sequence
<220> FEATURE:
<223> OTHER INFORMATION: hydrolysis probe
<220> FEATURE:
<221> NAME/KEY: misc_feature
<222> LOCATION: (1)..(1)
<223> OTHER INFORMATION: fluorescent tag 6FAM
<220> FEATURE:
<221> NAME/KEY: misc_feature
<222> LOCATION: (26)..(26)
<223> OTHER INFORMATION: fluorescent tag BHQ1

<400> SEQUENCE: 4
ggactctgga atccattctg gtgcca                                        26

<210> SEQ ID NO 5
<211> LENGTH: 19
<212> TYPE: DNA
<213> ORGANISM: Homo sapiens

<400> SEQUENCE: 5
gagtgaagga ctgagaaaa                                                19

<210> SEQ ID NO 6
<211> LENGTH: 18
<212> TYPE: DNA
<213> ORGANISM: Homo sapiens

<400> SEQUENCE: 6
ctgatttgat ggagttgg                                                 18

<210> SEQ ID NO 7
<211> LENGTH: 51
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(33)
<223> OTHER INFORMATION: non-complementary accessory tag
<220> FEATURE:
<221> NAME/KEY: misc_feature
<222> LOCATION: (34)..(51)
<223> OTHER INFORMATION: CTNNB1 sequence

<400> SEQUENCE: 7
tcgtcggcag cgtcagatgt gtataagaga caggcagcaa cagtcttacc t            51
```

```
<210> SEQ ID NO 8
<211> LENGTH: 58
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(34)
<223> OTHER INFORMATION: non-complementary accessory tag
<220> FEATURE:
<221> NAME/KEY: misc_feature
<222> LOCATION: (35)..(58)
<223> OTHER INFORMATION: CTNNB1 sequence

<400> SEQUENCE: 8
gtctcgtggg ctcggagatg tgtataagag acagctgtgt gctcttcgtg tgtggtgt        58

<210> SEQ ID NO 9
<211> LENGTH: 14
<212> TYPE: DNA
<213> ORGANISM: Artificial Sequence
<220> FEATURE:
<223> OTHER INFORMATION: Synthesized

<400> SEQUENCE: 9
tcgtcggcag cgtc                                                        14

<210> SEQ ID NO 10
<211> LENGTH: 16
<212> TYPE: DNA
<213> ORGANISM: Artificial Sequence
<220> FEATURE:
<223> OTHER INFORMATION: Synthesized

<400> SEQUENCE: 10
gtctcgtggg ctcgga                                                      16

<210> SEQ ID NO 11
<211> LENGTH: 51
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(33)
<223> OTHER INFORMATION: non-complementary accessory tag
<220> FEATURE:
<221> NAME/KEY: misc_feature
<222> LOCATION: (34)..(51)
<223> OTHER INFORMATION: hTERT sequence

<400> SEQUENCE: 11
tcgtcggcag cgtcagatgt gtataagaga cagaggggct gggagggccc g               51

<210> SEQ ID NO 12
<211> LENGTH: 18
<212> TYPE: DNA
<213> ORGANISM: Homo sapiens

<400> SEQUENCE: 12
gacccctccc gggtcccc                                                    18

<210> SEQ ID NO 13
<211> LENGTH: 11
<212> TYPE: DNA
<213> ORGANISM: Artificial Sequence
```

```
<220> FEATURE:
<223> OTHER INFORMATION: BNA clamp
<220> FEATURE:
<221> NAME/KEY: misc_feature
<222> LOCATION: (2)..(2)
<223> OTHER INFORMATION: bridged nucleic acid
<220> FEATURE:
<221> NAME/KEY: misc_feature
<222> LOCATION: (4)..(4)
<223> OTHER INFORMATION: bridged nucleic acid
<220> FEATURE:
<221> NAME/KEY: misc_feature
<222> LOCATION: (5)..(5)
<223> OTHER INFORMATION: bridged nucleic acid
<220> FEATURE:
<221> NAME/KEY: misc_feature
<222> LOCATION: (6)..(6)
<223> OTHER INFORMATION: bridged nucleic acid
<220> FEATURE:
<221> NAME/KEY: misc_feature
<222> LOCATION: (7)..(7)
<223> OTHER INFORMATION: bridged nucleic acid
<220> FEATURE:
<221> NAME/KEY: misc_feature
<222> LOCATION: (8)..(8)
<223> OTHER INFORMATION: bridged nucleic acid
<220> FEATURE:
<221> NAME/KEY: misc_feature
<222> LOCATION: (10)..(10)
<223> OTHER INFORMATION: bridged nucleic acid
<220> FEATURE:
<221> NAME/KEY: misc_feature
<222> LOCATION: (11)..(11)
<223> OTHER INFORMATION: phosphorylation modification

<400> SEQUENCE: 13 gcccccctccg g                                                          11

<210> SEQ ID NO 14
<211> LENGTH: 15
<212> TYPE: DNA
<213> ORGANISM: Homo sapiens

<400> SEQUENCE: 14
ccgacccctc ccggg                                                       15

<210> SEQ ID NO 15
<211> LENGTH: 18
<212> TYPE: DNA
<213> ORGANISM: Artificial Sequence
<220> FEATURE:
<223> OTHER INFORMATION: hydrolysis probe
<220> FEATURE:
<221> NAME/KEY: misc_feature
<222> LOCATION: (1)..(1)
<223> OTHER INFORMATION: fluorescent tag 6FAM
<220> FEATURE:
<221> NAME/KEY: misc_feature
<222> LOCATION: (18)..(18)
<223> OTHER INFORMATION: fluorescent tag BHQ1

<400> SEQUENCE: 15 cggaggggc tgggccgg                                                     18

<210> SEQ ID NO 16
<211> LENGTH: 18
<212> TYPE: DNA
<213> ORGANISM: Artificial Sequence
<220> FEATURE:
<223> OTHER INFORMATION: hydrolysis probe
<220> FEATURE:
<221> NAME/KEY: misc_feature
<222> LOCATION: (1)..(1)
```

```
<223> OTHER INFORMATION: fluorescent tag 6FAM
<220> FEATURE:
<221> NAME/KEY: misc_feature
<222> LOCATION: (18)..(18)
<223> OTHER INFORMATION: fluorescent tag BHQ1

<400> SEQUENCE: 16
cggaaggggc tgggccgg                                                      18
```

KIT AND METHOD FOR DETECTING MUTATIONS IN CTNNB1 AND HTERT, AND USE THEREOF IN HCC DETECTION AND DISEASE MANAGEMENT

CROSS-REFERENCE TO RELATED APPLICATION

The present application claims priority to U.S. Provisional Application No. 62/325,457, filed on Apr. 20, 2016, which is hereby incorporated by reference in its entirety.

GOVERNMENT SUPPORT

This invention was made with government support under R43CA165312 and R44CA165312 awarded by the National Institute of Health. The government has certain rights in the invention.

REFERENCE TO SEQUENCE LISTING SUBMITTED ELECTRONICALLY

The content of the electronically submitted sequence listing, file name HCC_Seq_list.txt, size 5,715 bytes; and date of creation Apr. 20, 2017, filed herewith, is incorporated herein by reference in its entirety.

FIELD OF THE INVENTION

The present disclosure relates generally to the field of biotechnology, and more specifically to early molecular cancer detection and disease management, including detecting and quantitatively measuring mutations and methylation in nucleic acid sequences associated with cancer using samples from tissues and biological fluids, and in more particular to a method for screening, detection and disease management of the hepatocellular carcinoma (HCC).

BACKGROUND

Hepatocellular carcinoma (HCC) is an aggressive malignancy that has a survival rate of 14% (Simard, Ward et al. 2012, American Cancer Society 2017). HCC is the fifth most common cancer in the world, and is the second leading cause of cancer mortality, responsible for between 250,000 and 800,000 deaths per year (Howlader N 2016). Most HCC patients are diagnosed at a late stage using conventional methods of detection, with a survival rate less than 5% after the diagnosis and subsequent treatment. The prognosis is much better if HCC patients are diagnosed at an early stage and treated with surgical and chemotherapeutic intervention. Unfortunately, the early stage of liver cancer is mostly asymptomatic, making the early detection of liver cancer a challenge.

Current methods in detecting HCC include monitoring high risk groups, such as those infected with HBV or HCV, with regular (usually annual or biannual) physical examinations, serum liver function tests (LFTs), ultrasound and other imaging studies. These methods all have their shortcomings. For example, ultrasound imaging is not sensitive for detecting small liver lesions. Other imaging methods, such as CT scan and MRI scan, are very expensive and submit patients to radiation exposure, prohibiting routine use of such methods.

In addition to imaging techniques, elevated serum concentrations of alpha-fetoprotein (AFP) is a useful surrogate marker for HCC, because on an average 50% of HCC patients have an elevated AFP level at the time of diagnosis. However, the elevated level of AFP is influenced by and can result from a number of non-malignant conditions. It is nearly impossible to detect HCC sufficiently early using current methods. Thus, there is a clear and urgent need for non-invasive, sensitive, reliable methods for the early detection of HCC (Bruix and Sherman 2011).

The high mortality rate of HCC (where 85% of patients die within 5 years) is mainly due to late detection and a high recurrence rate (Sherman 2008, Kamiyama, Nakanishi et al. 2009, Hung, Wong et al. 2016). Rates of recurrence range from 15% for liver transplantation to nearly 100% for surgery or ablation. Recurrence is most common within 2 years.

The high HCC recurrence rate can be attributed to (1) incomplete treatment, (2) micro-metastases within the liver, and (3) de novo lesions (Sherman 2008).

The early detection of recurrent HCC has been difficulty with the currently available diagnostic methods and serial imaging (Kamiyama, Nakanishi et al. 2009, Minami and Kudo 2015). Notably, there are no specific guidelines addressing how HCC recurrence should be monitored. MRI/CT imaging is the gold standard for diagnosis, although it is expensive and has limited utility in the detection of small tumors (<2 cm), tumors in the presence of previously treated lesions (especially from local ablation), cirrhosis, obesity, and dysplastic nodules (Willatt, Hussain et al. 2008, Minami, Nishida et al. 2014, Minami and Kudo 2015). Thus, there is an urgent unmet medical need to have a sensitive test for monitoring HCC recurrence.

SUMMARY

In a first aspect, the present disclosure provides a kit for characterizing, in a biological sample containing at least one first allele of a gene, at least one second allele in a genomic region of the gene. The kit comprises a first pair of primers and at least one clamp. The first pair of primers are configured to specifically bind sequences flanking the genomic region to thereby allow amplification of at least one polynucleotide harboring the genomic region in a first PCR reaction; and each of the at least one clamp is configured to bind to one of the at least one first allele but not any of the at least one second allele at an annealing temperature in the first PCR reaction to thereby selectively suppress amplification of the one of the at least one first allele but still allow amplification of the at least one second allele.

Herein the genomic region can be a mutation hotspot where multiple mutation sites are concentrated in the mutation hotspot, such as hotspot region 1 of the CTNNB1 gene, which corresponds to codon 32-37 of β-catenin protein (encoded by CTNNB1), but the genomic region can be a short region that covers one mutation. Herein "characterizing" can be "detecting/identifying" or "quantifying", etc. Herein, the "clamp" can be a bridged nucleic acid (BNA) clamp, a locked nucleic acid (LNA) clamp, or any other molecule that can selectively bind to, thus clamp, one or more first allele to be suppressed for amplification while does not clamp one or more second allele to be allowed for amplification in the first PCR reaction.

The kit can further comprise a second pair of primers and at least one probe, which are configured to allow characterization of one or more of the at least one second allele in a second PCR reaction over the at least one polynucleotide. Herein the second PCR reaction can be a real-time PCR, or a quantitative PCR, etc., and the probe can be a hydrolysis probe (such as a fluorescent probe) that allows for quantification purpose for the second PCR reaction.

According to some embodiments, at least one of the first pair of primers comprises an oligonucleotide of an artificial sequence at a 5'-end thereof and is configured to interrupt a secondary structure of DNA molecules of the gene or to increase a Tm of the at least one of the first pair of primers in the first PCR reaction using amplified products as templates to thereby increase an efficiency of the amplification of the at least one polynucleotide in the first PCR reaction.

In some embodiments of the kit, the gene is CTNNB1, the genomic region is hotspot region 1 encoding codons 32-37 of CTNNB1, the at least one first allele comprises a wildtype allele of CTNNB1 in hotspot region 1, the at least one second allele comprises one or more mutant alleles of CTNNB1 in hotspot region 1, and the at least one clamp comprises a bridged nucleic acid (BNA) clamp specifically targeting the wildtype allele of CTNNB1. For the first PCR reaction, the BNA clamp can have a nucleotide sequence as set forth in SEQ ID NO: 3, and the first pair of primers can respectively have a nucleotide sequence as set forth in SEQ ID NO: 1 and SEQ ID NO: 2. For the second PCR reaction, the probe can be a hydrolysis probe having a nucleotide sequence as set forth in SEQ ID NO: 4, which is configured to allow detection or quantification of the one or more mutant alleles of CTNNB1 in a second PCR reaction over the at least one polynucleotide obtained from the first PCR reaction.

In some other embodiments of the kit, the gene is hTERT, the genomic region comprises nucleotide position −129 to −119 upstream from a start codon of hTERT, the at least one first allele comprises a wildtype allele of hTERT, the at least one second allele comprises one or more mutant alleles of hTERT in the genomic region, and the at least one clamp comprises a bridged nucleic acid (BNA) clamp specifically targeting the wildtype allele of hTERT. To increase PCR efficiency, the kit can further include DMSO, which can have a concentration of ~5% in the first PCR reaction. For the first PCR reaction, the BNA clamp can have a nucleotide sequence as set forth in SEQ ID NO: 13, and the first pair of primers can respectively have a nucleotide sequence as set forth in SEQ ID NO: 11 and SEQ ID NO: 12. For the second PCR reaction, the probe can be a hydrolysis probe having a nucleotide sequence as set forth in SEQ ID NO: 15 or SEQ ID NO: 16, which are configured to respectively allow detection or quantification of the wildtype allele or any of the one or more mutant alleles of hTERT in a second PCR reaction over the at least one polynucleotide obtained from the first PCR reaction. Additionally, a third pair of primers respectively having a nucleotide sequence as set forth in SEQ ID NO: 11 and SEQ ID NO: 14 can be included in the kit, which are configured to be employed in the second PCR reaction.

In a second aspect, the present disclosure further provides a method for characterizing, in a biological sample containing at least one first allele of a gene, at least one second allele in a genomic region of the gene, by means of the kit as described above.

The method comprises step (a): performing the first PCR reaction over a mixture of the biological sample, the first pair of primers, and the at least one clamp to thereby obtain a first PCR product. Step (a) can comprise a sub-step of annealing the mixture at an annealing temperature for a time period such that each of the at least one clamp binds to one of the at least one first allele but not any of the at least one second allele to thereby selectively suppress amplification of the one of the at least one first allele but still allow amplification of the at least one second allele.

The method can further comprise step (b): performing a second PCR reaction over the first PCR product by means of a second pair of primers and at least one probe to allow characterization of one or more of the at least one second allele.

In some embodiments of the method, the second PCR reaction in step (b) is configured to quantify one or more of the at least one second allele. As such, a first cycle number for the first PCR reaction and a second cycle number for the second PCR reaction are configured to avoid non-specific amplification and to ensure amplification is within a range of linearity.

In some embodiments of the method, the gene is CTNNB1, the genomic region is hotspot region 1 encoding codons 32-37 of CTNNB1, the at least one first allele comprises a wildtype allele of CTNNB1 in hotspot region 1, the at least one second allele comprises one or more mutant alleles of CTNNB1 in hotspot region 1, the first pair of primers respectively have a nucleotide sequence as set forth in SEQ ID NO: 1 and SEQ ID NO: 2, and the at least one clamp comprises a bridged nucleic acid (BNA) clamp having a nucleotide sequence as set forth in SEQ ID NO: 3. Accordingly, in the sub-step of annealing the mixture at an annealing temperature for a time period in the first PCR reaction, the annealing temperature can have a range of 52-56° C. In order to quantify CTNNB1 mutations, the method includes step (b): performing a second PCR reaction over the first PCR product by means of a second pair of primers and a probe, respectively having nucleotide sequences as set forth in SEQ ID NO: 1, SEQ ID NO: 2, and SEQ ID NO: 4.

In some other embodiments of the method, the gene is hTERT, the genomic region comprises nucleotide position −129 to −119 upstream from a start codon of hTERT, the at least one first allele comprises a wildtype allele of hTERT, the at least one second allele comprises one or more mutant alleles of hTERT in the genomic region, the first pair of primers respectively have a nucleotide sequence as set forth in SEQ ID NO: 11 and SEQ ID NO: 12, and the at least one clamp comprises a bridged nucleic acid (BNA) clamp having a nucleotide sequence as set forth in SEQ ID NO: 13. Accordingly, in the sub-step of annealing the mixture at an annealing temperature for a time period in the first PCR reaction, the annealing temperature can have a range of 78-82° C. In order to quantify hTERT mutation(s), the method includes step (b): performing a second PCR reaction over the first PCR product by means of a second pair of primers and a probe, wherein the second pair of primers respectively have a nucleotide sequences as set forth in SEQ ID NO: 11 and SEQ ID NO: 14; and the probe has a nucleotide sequence as set forth in SEQ ID NO: 15 or SEQ ID NO: 16, configured to respectively allow detection or quantification of the wildtype allele or any of the one or more mutant alleles of hTERT.

In a third aspect, the disclosure further provides a method of detecting or monitoring a recurrence of hepatocellular carcinoma (HCC), in a DNA sample obtained from a biological sample of a subject in need thereof. The method comprises the step of: (i) determining a level of mutation or methylation of one or more genes from a group consisting of TP53, CTNNB1, hTERT, RASSF1A, and GSTP1 in the biological sample; and (ii) detecting a presence or an absence of HCC based on the level of mutation or methylation of the one or more genes.

Herein the biological sample can be an tissue sample, such as a biopsy sample, or can be a blood, serum, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid or cytoplasm and lymph, bronchial secretions, mucus, or vitreous or aqueous humor. A particularly useful biological sample in the present disclosure is urine sample.

According to some embodiments, step (i) comprises determining a level of mutation of CTNNB1 in the biological sample, which comprises the sub-steps of:

performing a first PCR reaction over a mixture of the biological sample, a first pair of primers, and a clamp to thereby obtain a first PCR product, wherein the first pair of primers and the clamp respectively have a nucleotide sequence as set forth in SEQ ID NO: 1, SEQ ID NO: 2, and SEQ ID NO: 3; and performing a second PCR reaction over the first PCR product by means of a second pair of primers and a probe to determine the level of mutation of CTNNB1, wherein the second pair of primers and the probe respectively have a nucleotide sequence as set forth in SEQ ID NO: 1, SEQ ID NO: 2, and SEQ ID NO: 4.

Herein the biological sample can be a urine sample, and step (ii) can comprise: detecting a presence of HCC, if the level of mutation of CTNNB1 in the urine sample is more than or equal to 10 copies of mutated CTNNB1 per 1,000 copies of CTNNB1 gene.

According to some other embodiments, step (i) comprises: determining a level of mutation of hTERT in the biological sample, which comprises the sub-steps of:

performing a first PCR reaction over a mixture of the biological sample, a first pair of primers, and a clamp to thereby obtain a first PCR product, wherein the first pair of primers and the clamp respectively have a nucleotide sequence as set forth in SEQ ID NO: 11, SEQ ID NO: 12, and SEQ ID NO: 13; and performing a second PCR reaction over the first PCR product by means of a second pair of primers and a probe to determine the level of mutation of hTERT, wherein the second pair of primers and the probe respectively have a nucleotide sequence as set forth in SEQ ID NO: 11, SEQ ID NO: 14, and SEQ ID NO: 16.

Herein the biological sample can be a urine sample, and step (ii) can comprise: detecting a presence of HCC, if the level of mutation of hTERT in the urine sample is more than or equal to 20 copies of mutated hTERT per 1,000 copies of hTERT gene.

According to some embodiments of the method, step (i) comprises: determining a level of mutation or methylation of each of TP53, CTNNB1, hTERT, RASSF1A, and GSTP1 in the biological sample; and step (ii) comprises: detecting a presence or an absence of HCC based on the level of mutation or methylation of each of TP53, CTNNB1, hTERT, RASSF1A, and GSTP1 in the biological sample.

According to some other embodiments of the method, step (i) further comprises: determining a level of alpha-fetoprotein (AFP) in the biological sample; and step (ii) comprises: detecting a presence or an absence of HCC based on the level of mutation or methylation of each of TP53, CTNNB1, hTERT, RASSF1A, and GSTP1, and the level of AFP, in the biological sample.

BRIEF DESCRIPTION OF THE DRAWINGS

FIG. 2(A) shows the primers that were designed flanking the hotspot region 1 in the presence of a BNA clamp that targets this hotspot region (step 1). The amplified product from step 1 was then analyzed by qPCR with a hydrolysis probe that targets hotspot region 1 (step 2). FIG. 2(B) shows the amplification and standard curves of the reconstituted standards and controls in the BNA clamp mediated CTNNB1 32-37 mutation qPCR assay. Curves were generated with varying dilutions of the pCTNNB1_S37C plasmid in a background of wild-type sonicated Hep3B cell line DNA. Analysis was carried out using Roche LightCycler® 480 software.

FIGS. 3A-B show the analysis of CTNNB1 mutation in liver diseased tissue samples. FIG. 3(A) shows the distribution of percent CTNNB1 hotspot mutation obtained by the CTNNB1 32-37 mutation qPCR assay in liver tissues of patients with HCC, hepatitis, and cirrhosis. FIG. 3(B) shows the validation of CTNNB1 32-37 mutation qPCR assay by Sanger sequencing. 11 of the 18 samples testing positive by the qPCR assay were randomly selected and evaluated by Sanger sequencing. Of these samples, 4/11 had detectable CTNNB1 mutation. To enrich or the mutation, Sanger sequencing was repeated using BNA in the PCR amplification of these 11 samples. Sanger sequencing with BNA confirmed 3 additional samples. Sample A35K could not be amplified with BNA.

FIG. 4(A) shows agarose gel electrophoresis of 30 ng of intact genomic and fragmented genomic SNU398 DNA. The SNU398 genomic DNA was fragmented through sonication, giving rise to 200-500 bp genomic fragments. (B) Comparison of the quantity of mutated CTNNB1 in the intact and fragmented genomic SNU398 DNA to pCTNNB1_S37C in a background of Human genomic DNA (3 ng), which was the standard used for quantification by the CTNNB1 32-37 mutation qPCR assay. The SNU398 cell line is heterozygous for the S37C mutation. Compared side by side, the fragmented cell line was 7-times overestimated over the intact genomic DNA. Sonicated genomic DNA is approximately 3-times overestimated, and intact genomic DNA is approximately 2.2-times underestimated by the plasmid standards.

FIG. 6(A) shows primers that were designed flanking the hotspot region 1 in the presence of a BNA clamp that targets this hotspot region (step 1). The amplified product from step 1 was then analyzed by qPCR with a hydrolysis probe that targets the −124 G/A mutation (step 2). FIG. 6(B) shows amplification and standard curves of the standards in the BNA clamp mediated hTERT mutation assay. Curves were generated with varying dilutions of the sonicated SNU398 cell line (known −124 G/A mutation) in reconstituted sonicated Hep3B cell line.

FIG. 7(D) provides univariate receiver operating curves for serum AFP (top) and TP53 249T (bottom), FIG. 7(E) provides univariate receiver operating curves for mRASSF1A (top) and mGSTP1 (bottom), FIG. 7(F) provides univariate receiver operating curves for CTNNB1 (top) and hTERT (bottom) hotspot mutations.

DETAILED DESCRIPTION OF THE INVENTION

Figure 1:
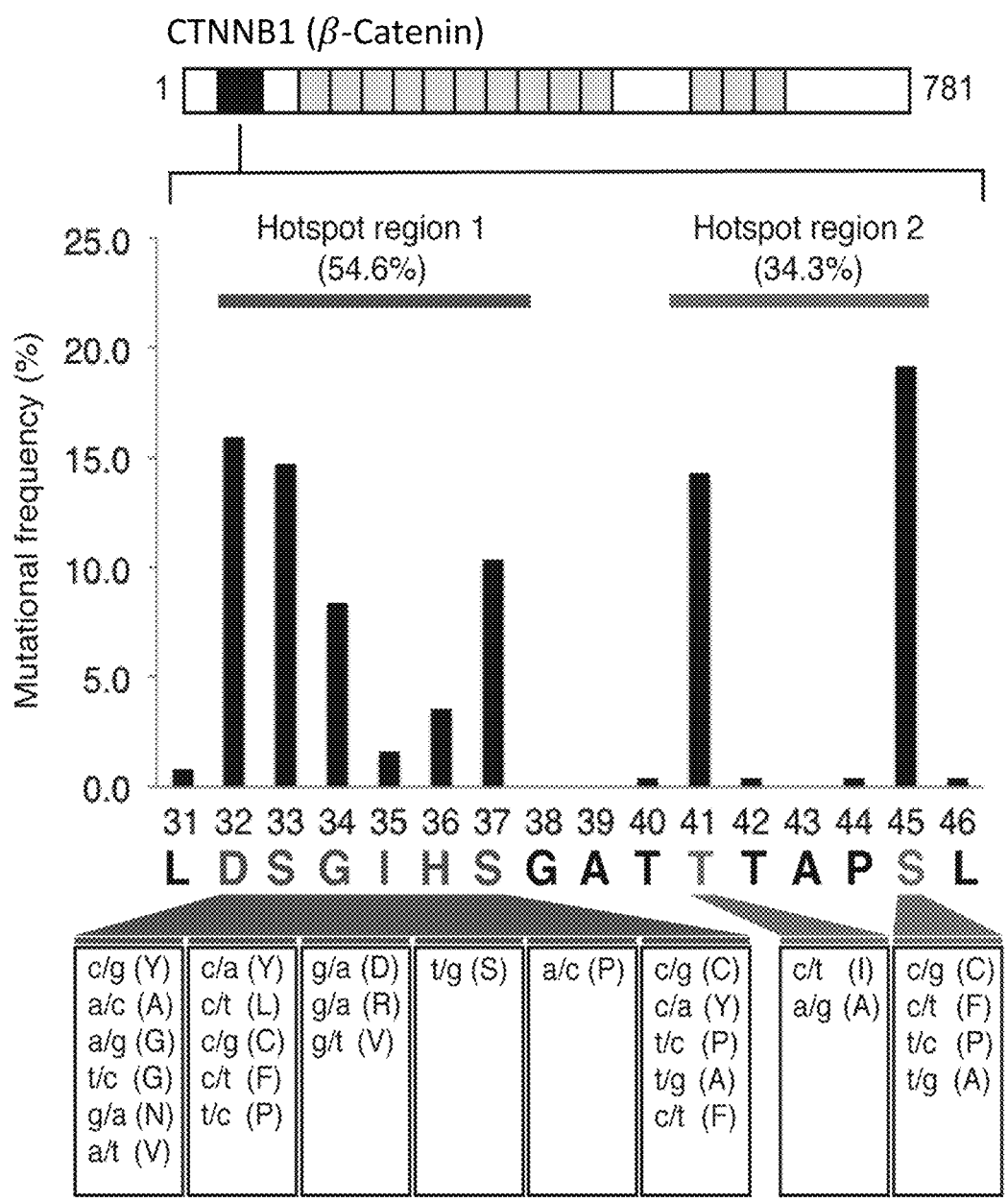
FIG. 1 shows a schematic of the CTNNB1 (encoding β-catenin) exon 3 mutational frequencies associated with HCC: Data from several studies that have sequenced CTNNB1 exon 3 in patients with HCC was compiled and is depicted in this graph. Nearly 90% of all HCC tumors with a mutation in CTNNB1 reside within one of two hotspot regions: region 1 (codons 32-37; 54.6%) and region 2 (codons 41-45; 34.3%). The X-axis denotes the codon number in exon 3 of CTNNB1 gene and the amino acid encoded by it is indicated below. The box linked to the indicated amino acid lists the reported missense mutations within the codon and the corresponding amino acid.

Disclosed herein is a sensitive, specific, and quantitative test for early detection of cancer.

Circulating cell-free DNA (cfDNA) has been identified in biological fluids (Anker, Lyautey et al. 2001, Chan, Chiu et al. 2003, Diehl, Schmidt et al. 2008). For example, in urine, two species are seen: a high-molecular-weight (HMW) DNA, greater than 1 kb, derived mostly from sloughed off cell debris from the urinary tract, and a low-molecular-weight (LMW) DNA, approximately 150 to 250 base pairs (bp), derived primarily from apoptotic cells (Su, Wang et al. 2004).

It has been demonstrated that urine containing fragmented cfDNA. This urine fragmented DNA can be used for detection of cancer-related DNA markers, if a tumor is present (Su, Wang et al. 2004, Su, Wang et al. 2005, Su, Wang et al. 2008, Lin, Dhillon et al. 2011, Song, Jain et al. 2012). CTNNB1 hotspot mutations and hTERT promoter mutations have been suggested to be useful and appropriate for detection of tumor presence.

More specifically, the disclosure relates to detecting HCC in a subject by determining the level of mutation and methylation of a panel of genes comprising DNA markers for the early detection of HCC, monitoring HCC recurrence, and for disease management. The development of HCC, as with other solid tumors, is believed to require the dysregulation of at least 3 biochemical pathways (proliferation, cell cycle, apoptosis/cell survival) within the cell (Pepe and Thompson 2000, Zhang, Yu et al. 2007, Gerszten and Wang 2008). In addition to genetic mutations, the aberrant methylation of tumor suppressors plays important roles throughout the process of HCC carcinogenesis. Thus, the urine DNA panel test is designed to detect both genetic mutations including TP53 mutation, CTNNB1 hotspot mutations, hTERT mutations (Nault, Mallet et al. 2013), and epigenetic methylated DNA markers including mRASSF1A (Nishida, Nagasaka et al. 2008, Newell, Toffanin et al. 2009), and mGSTP1 (Yang, Guo et al. 2003, Nomoto, Kinoshita et al. 2007, Harder, Opitz et al. 2008, Nishida, Nagasaka et al. 2008), to obtain sufficient sensitivity and specificity for HCC screening, detection, and disease management.

Mutations arising in the CTNNB1 gene have been associated with many cancers, often presenting in nearly 10-40% of all cases. In HCC, mutations in the CTNNB1 gene occur in nearly 20-40% of all cases, and the majority are found in a hotspot region of codons 32-37. Current methods to detect CTNNB1 mutations rely mainly on PCR-based assays followed by DNA sequencing, which is insensitive, time consuming and labor intensive. Thus, a need exists for quantitative measurements of CTNNB1 hotspot mutations that is robust and reliable to serve as a screening test for early detection of HCC.

Somatic mutations in the hTERT promoter region have been reported in several tumor types. hTERT mutations are most frequently observed −124 nt from the ATG start site, as a G/A or G/T substitution. Downstream consequences of altered hTERT transcription are unknown, although this mutation is believed to be one of the most frequently occurring in HCC. Current methods rely mainly on PCR-based assays followed by DNA sequencing, and a need exists for quantitative measurements of hTERT mutations that is robust and reliable to serve as a screening test for early detection of HCC.

There remains a need for a method to more consistently and accurately determine the mutation level of the CTNNB1 gene and the mutation level of the hTERT gene for HCC screening, early disease detection, and disease management. There also remains a need for whether the mutated DNA derived from HCC can be detected in urine, plasma or other body fluids.

The present subject matter may be understood more readily by reference to the following detailed description taken in connection with the accompanying examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it is understood that the particular value forms another embodiment. All ranges are inclusive and combinable.

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "genome" and "genomic" refer to any nucleic acid sequences (coding and non-coding) originating from any living or non-living organism or single-cell. These terms also apply to any naturally occurring variations that may arise through mutation or recombination through means of biological or artificial influence. An example is the human genome, which is composed of approximately $3 \times 10^9$ base pairs of DNA packaged into chromosomes, of which there are 22 pairs of autosomes and 1 allosome pair.

The term "nucleotide sequence" as used herein indicates a polymer of repeating nucleic acids (Adenine, Guanine, Thymine, and Cytosine, and Uracil) that is capable of base-pairing with complement sequences through Watson-Crick interactions. This polymer may be produced synthetically or originate from a biological source.

The term "nucleic acid" refers to a dexoyribonucleotide (DNA) or ribonucleotide (RNA) and complements thereof. The size of nucleotides is expressed in base pairs "bp". Polynucleotides are single- or double stranded polymers of nucleic acids and complements thereof.

The term "deoxyribonucleic acid" and "DNA" refer to a polymer of repeating deoxyribonucleic acids.

The term "ribonucleic acid" and "RNA" refer to a polymer of repeating ribonucleic acids.

A biological fluid can comprise, for example, whole tissue, such biopsy sample. Other examples of a biological fluid include, but are not limited to, saliva, nasopharyngeal, blood, plasma, serum, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid or cytoplasm and lymph. bronchial secretions, mucus, or vitreous or aqueous humor. Biological fluid can also include a culture medium. A particularly useful biological fluid in the present method is urine.

As used herein, "cancer" refers to any stage of abnormal growth or migration of cells or tissue, including precancerous and all stages of cancerous cells, including but not limited to adenomas, metaplasias, heteroplasias, dysplasias, neoplasias, hyperplasias, and anaplasias.

The term "biomarker" is an agent used as an indicator of a biological state. It can be a characteristic that is objectively measured and evaluated as an indicator of normal biological processes, pathogenic processes, or pharmacologic responses to a therapeutic intervention. A biomarker can be a fragment of genomic DNA sequence that causes disease or is associated with susceptibility to disease, and may or may not comprise a gene.

In certain embodiments, a platform uses biological samples containing fragmented circulation derived DNA known as "low molecular weight" (LMW) DNA. The DNA is low molecule weight because it is generally less than 300 base pairs in size. This LMW DNA is released into circulation through necrosis or apoptosis by both normal and cancer cells. It has been shown that LWM DNA is excreted into the urine and can be used to detect tumor-derived DNA, provided a suitable assay, such as a short template assay for which detection is available (Su, Song et al. 2008). Based on the present discovery of how to modify LMW nucleic acid sequences to prevent amplification of the wildtype sequences in a nucleotide amplification reaction assay, LMW DNA from biological samples, for example urine, can be compared to wildtype control DNA with a high degree of specificity.

A "locked nucleic acid" LNA is a chemically modified RNA nucleotide whose ribose is modified with a methylene bridge connecting the 2'-oxygen and 4'-carbon.

A "bridged nucleic acid" BNA is a chemically modified RNA nucleotide whose ribose is modified with an aminoethylene bridge connecting the 2'-oxygen and 4'-carbon.

The term "nucleotide amplification reaction" refers to any suitable procedure that amplifies a specific region of polynucleotides (target) using primers.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "effective amount," in the context of treatment of a disease or disorder refers to the amount of such molecule that is sufficient to inhibit the occurrence or ameliorate one or more clinical or diagnostic symptoms of the disease or disorder in a subject. The term "effective regime" refers to a combination of amount of the agent being administered and dosage frequency adequate to accomplish treatment or prevention of the disease or disorder.

Due to the imprecision of standard analytical methods, molecular weights and lengths of polymers are understood to be approximate values. When such a value is expressed as "about" X or "approximately" X, the stated value of X will be understood to be accurate to ±10%.

Examples are provided to assist in a further understanding of the inventions. Particular materials used, protocols and conditions are intended to be further illustrative of the inventions and should not be construed to limit the reasonable scope thereof.

The disclosure includes methods to noninvasively detect levels of mutations or methylation of a panel of genes for HCC screening, cancer progression, and for HBV disease monitoring.

Provided herein is a method for detecting the presence or absence of a cancer in an individual by determining the level of mutation and methylation of a panel of genes from the individual, comparing the level of mutation and methylation with a baseline level of mutation and methylation found in one or more control samples from individuals known not to have the cancer, and correlating a finding of elevated mutation or methylation in the individual with an enhanced likelihood that the individual has cancer. The cancer can be hepatocellular carcinoma (HCC) and the control can be non-HCC. The tumor-associated genes can be TP53, CTNNB1, hTERT, RASSF1A, and GSTP1. The regulatory region can be the promoter of the hTERT, RASSF1A and GSTP1 genes, the first exon of the RASSF1A and GSTP1 genes, or both. The individual can be a human.

Also described herein is a method providing a sensitive, specific, and quantitative assay for detecting mutations in the codon 32-37 region of exon3 of the CTNNB1 gene, using isolated nucleic acid sequences compared to wildtype CTNNB1 sequences from a biological sample such as a tissue or a body fluid. Any tumor-derived DNA isolated from patients can be used in the present method because of selective amplification of mutated DNA sequences but not wildtype sequence in a nucleotide amplification reaction such as PCR. The method uses a seventeen nucleotide bridged nucleic acid (BNA) clamp designed to suppress the amplification of wildtype sequences; amplifying selective CTNNB1 templates that do not contain any mismatches with the BNA clamp. The PCR product was quantified by a hydrolysis probe in the second step PCR. The running time of the assay is approximately 6 hours and can be used daily as a high throughput format for a blood or urine test for HCC screening. For areas with a low prevalence of the mutation, this screening assay may be combined with other complementary screening tests such as the alpha-fetoprotein blood test and ultrasound imaging. The cutoff CTNNB1 mutation level for detecting HCC can be at 10 copies of mutated CTNNB1 per mL of urine.

Also described herein is a process to quantify the amount of mutated nucleic acid in the CTNNB1 codons 32-37 region. The first step of the two-step PCR assay targets a small amplicon using primers of the nucleotide sequence as set forth in SEQ ID NO: 1 and SEQ ID NO: 2 in addition to a BNA clamp, SEQ ID NO: 3, which is used to suppress the amplification of a wildtype DNA template. For the second PCR step primers used for amplification include the nucleotide sequence as set forth in SEQ ID NO: 1 and SEQ ID NO: 2, in addition to a hydrolysis probe, SEQ ID NO: 4, that detects the region of codons 32-37. The assay has high sensitivity and specificity. The BNA clamp-mediated PCR assay detects up to a few copies of the mutated sequence with a high specificity ratio of 1:1,000 (0.1%) of mutant to wildtype sequences. The suppression of wildtype template amplification by the BNA clamp is based on the perfect match of the BNA clamp to the wildtype sequences. The base pairing of BNA to DNA exerts higher thermostability than that of DNA to DNA, resulting in a wide range of Tm differences (6-10° C.) between the perfect match and a single base pair mismatch. Based on the Tm difference the inventors optimized the PCR conditions to selectively amplify only the mutated sequence and not the wildtype sequence. Of importance, the assay is able to detect any mutation in the region of codons 32-37 of CTNNB1.

In addition to high sensitivity and specificity, the process also achieved accurate quantification of the mutated nucleic acid in CTNNB1 codon 32-37 region. For at least the three reasons that follow, quantification of the mutated nucleic acid is particularly difficult: (1) it is difficult to determine the cycle numbers for the first round PCR to ensure within-linear-range amplification after two steps of amplification; (2) the cycle numbers for the second round PCR needs to be precise in order to avoid non-specific amplification and to ensure the amplification is within the range of linearity; and (3) a degree of secondary structure is thought to exist in this region presenting unique challenges for amplification. The addition of artificial tag sequences at the 5' end of the SEQ ID NO: 2 enabled the successful PCR amplification of the sequences of interest, because of (1) increase of the Tm of the primer to the templates generated from PCR reaction resulting high efficiency of amplification and (2) potential interference of the secondary structure formation of the templates.

The methods described herein can be used to determine the status of existing disease identified in a subject. For example, when 13 urine samples that were positive for CTNNB1 hotspot mutation were tested, 7 of these samples showed that the detected CTNNB1 mutation was undetectable after the HCC was surgically removed. The other 6 patients all had recurrence. Thus, mutations detected in the urine collected before and after the surgery can be tested to determine if the status of the patient has changed by evaluating whether LMW nucleic acid with the mutation is no longer detectable in the urine collected after the surgical removal of HCC tumor.

Also described herein is a method providing a sensitive, specific, and quantitative assay for detecting mutations in the promoter region of the hTERT gene located nt. −129 to −119 upstream of the ATG start codon, using isolated nucleic acid sequences compared to wildtype hTERT sequences from a biological samples including body fluid. Any tumor-derived DNA isolated from patients can be used in the present method because of selective amplification of mutated DNA sequences but not wildtype sequence in a nucleotide amplification reaction such as PCR. The method uses an eleven nucleotide BNA clamp designed to suppress the amplification of wildtype sequences; amplifying selective hTERT templates that do not contain any mismatches with the BNA clamp. The PCR product was quantified by a hydrolysis probe in the second-step PCR reaction. The running time of the assay is approximately 6 hours and can be used daily as a high throughput format for a blood or urine test for HCC screening. For areas with a low prevalence of the mutation, this screening assay may be combined with other complementary screening tests such as the alpha-fetoprotein blood test and ultrasound imaging. The cutoff hTERT mutation level for detecting HCC can be at 20 copies of mutated hTERT per mL of urine.

Also described herein is a process to quantify the amount of mutated nucleic acid in of hTERT promoter mutations. The first step of the two-step PCR assay targets a small amplicon using primers of the nucleotide sequence as set forth in SEQ ID NO: 11 and SEQ ID NO: 12 in addition to a BNA clamp, SEQ ID NO: 13, which is used to suppress the amplification of a wildtype DNA template. For the second PCR step primers used for amplification include the nucleotide sequence as set forth in SEQ ID NO: 11 and SEQ ID NO: 14, in addition to a hydrolysis probe, SEQ ID NO: 15 or SEQ ID NO: 16, that detects WT and −124 promoter mutant of hTERT, respectively. The assay has high sensitivity and specificity. The BNA clamp-mediated PCR assay detects up to a few copies of the mutated sequence with a high specificity ratio of 1:1,000 (0.1%) of mutant to wildtype sequences. The suppression of wildtype template amplification by the BNA clamp is based on the perfect match of the BNA clamp to the wildtype sequences. The base pairing of BNA to DNA exerts higher thermostability than that of DNA to DNA, resulting in a wide range of Tm differences (6-10° C.) between the perfect match and a single base pair mismatch. Based on the Tm difference the inventors invented and optimized the PCR conditions to selectively amplify only the mutated sequence and not the wildtype sequence. The PCR selectivity is achieved in the first step PCR of this two-step PCR assay. After a conventional 95° C. denaturing the templates, the reaction is followed by an annealing step (78-82° C.) for BNA to bind to wildtype templates, but not to mutated templates, and then followed by a combination step of primer annealing and extension at 70-74° C. This high primer annealing temperature was designed to keep the high GC content of amplified region (84% GC in this 50 basepair amplified region) templates in single-stranded denatured form for primers to anneal. In addition, 5% DMSO was added to overcome this extreme high GC content PCR reaction and the addition of artificial tag sequences at the 5' end of the SEQ ID NO: 11 enabled high efficient PCR amplification of the sequences of interest, because of the increase of the Tm of the primer to the templates generated from PCR reaction.

The methods described herein can be used to identify subject patients for treatment and to determine risk factors associated with specific mutant CTNNB1 or mutant hTERT associated cancers. Such methods can include, for example, determining whether an individual has relatives who have been diagnosed with a particular disease. Screening methods can also include, for example, conventional work-ups to determine familial status for a particular disease known to have a heritable component. Screening may be implemented as indicated by known patient symptomology, age factors, related risk factors, etc. These methods allow the clinician to routinely select patients in need of the methods described herein for treatment. In accordance with these methods, screening may be implemented as an independent program or as a follow-up, adjunct, or to coordinate with other treatments. Thus, the methods as disclosed herein can be used for cancer screening, particularly for early detection, monitoring of recurrence, disease management, and to develop a personalized medicine regime for a cancer patient.

The performance of a 5-DNA marker panel (mRASSF1A, TP53, mGSTP1, CTNNB1, and hTERT) was tested alone or in combination with AFP, to distinguish HCC from cirrhosis and hepatitis and shown that DNA marker panel plus AFP detected 89% HCC at the specificity of 90% in the study cohort described in Table 1.

TABLE 1

Summary of the clinicopathological characteristics of the patients in the study cohort.

| Characteristics | HCC (n = 84) | Cirrhosis (n = 106) | Hepatitis (n = 97) |
| --- | --- | --- | --- |
| Mean age ± SD years | 59.3 ± 11.72 | 58.2 ± 10.9 | 52.43 ± 10.3 |
| Male/Female/Unknown | 63/21 | 72/34 | 58/38/1 |
| HBV/HCV/other | 46/21/17 | 34/50/22 | 55/43 |
| Stage 1/2/3/4/unknown | 25/35/19/2/3 | NA | NA |
| Grade 1/2/3/unknown | 9/51/21/3 | NA | NA |
| AFP levels, ng/mL, ±SD | 5669.0 ± 23,885 | 2.3 ± 2.3 | 7.3 ± 23.5 |

AFP, alpha-fetoprotein;
HBV, hepatitis B virus;
HCC, hepatocellular carcinoma;
HCV, Hepatitis C virus;
SD, standard deviation;
NA, Not applicable.

It is to be understood that the above described embodiments are merely illustrative of numerous and varied other embodiments which may constitute applications of the principles of the invention. Such other embodiments may be readily devised by those skilled in the art without departing from the spirit or scope of this invention and it is our intent they be deemed within the scope of our invention.

The invention is further illustrated by the following non-limiting examples.

Study Subjects and Methods

Samples, for this study were acquired under IRB (institutional review board) approval from the National Cheng-Kung University Medical Center in Taiwan, which provided 73 tissue samples from cancer patients who had undergone surgical resection, as well as noncancerous adjacent tissue to trace methylation throughout the pathology of HCC. Additional diseased tissue (35 hepatitis and 35 cirrhotic) was also obtained under IRB approval from the Buddhist Tzu Chi Medical center in Hualien, Taiwan. The clinicopathological characteristics of these samples are provided in Table 1. The urine samples were collected at the National Cheng-Kung University Medical Center in accordance with the guidelines of the institutional review board.

DNA Isolation from Tissue and Urine

Tissue DNA was isolated by using the Qiagen DNAeasy Blood and Tissue Kit™ (Qiagen, Valencia, Calif.) according to the manufacturer's instructions. The DNA concentration was measured using a Nanodrop 1000™ spectrophotometer (Thermo Fisher Scientific Inc, Wilmington, Del.) at 260 nm absorbance. The procedures for urine collection and urine DNA isolation were carried out as described previously (Lin, Dhillon et al. 2011). Briefly, 0.5 M EDTA, pH 8.0, was added to a fresh urine sample to a final concentration of 10 mM EDTA to inhibit possible nuclease activity and stored at −70° C. To isolate total urine DNA, the frozen urine sample was thawed at room temperature and then placed immediately in ice prior to DNA isolation. DNA was isolated from thawed urine within an hour. Urine samples were mixed with 1 volume of 6M guanidine thiocyanate by inverting 8 times. Then, 1 ml of resin (Wizard DNA purification kit, Promega, Madison, Wis.) was added to the urine lysate and incubated for 2 hours to overnight at room temperature with gentle mixing. The resin-DNA complex was centrifuged, transferred to a minicolumn (provided in the kit), and washed with a buffer provided by the manufacturer; the DNA was then eluted with Tris-EDTA buffer. The LMW urine DNA fractions were obtained using carboxylated magnetic beads (CMBs) (Agencourt Bioscience Corporation, Beverly, Mass.) and a binding method developed previously by our laboratory (Su, Song et al. 2008). Total urine DNA (resuspended in Tris-EDTA buffer) was mixed with 5 M NaCl and 20% polyethylene glycol 8000 (AMRESCO Inc., Solon, Ohio) to final concentrations of 0.3 M and 8%, respectively. The CMB suspension (Agencourt Bioscience Corporation) was washed and resuspended with Tris-EDTA buffer prior to use. Ten microliters of prewashed CMB suspension was added to the DNA mix and incubated for 1 to 2 hours at room temperature to allow binding of HMW DNA to the beads. The beads bound with HMW DNA were then removed from the suspension using a magnetic plate (Agencourt Bioscience Corporation). The LMW DNA remaining in the suspension was collected by adding 10 microliters of prewashed CMB in a solution of 1.2 M NaCl and 10% polyethylene glycol 8000. The beads bound with LMW or HMW DNA were then washed with 75% ethanol and the DNA was eluted in Tris-EDTA buffer.

Frequency of CTNNB1 Hotspot Mutations

The mutational frequency of the CTNNB1 gene in cancer is known to occur at a frequency from 10-40%. FIG. 1 shows a schematic of the CTNNB1 exon 3 mutational frequencies associated with HCC. Data from several studies that have sequenced CTNNB1 exon 3 in patients with HCC was compiled and is depicted in this graph. As shown in FIG. 1, nearly 90% of all HCC tumors with a mutation in CTNNB1 reside within one of two hotspot regions: region 1 (codons 32-37; 54.6%) and region 2 (codons 41-45; 34.3%).

DNA oligonucleotides used for the CTNNB1 hotspot mutation assay and hTERT promoter mutation assay. The primers, probes, and BNA clamp sequences that are used in the PCR assays claimed in this application, including the CTNNB1 hotspot mutation assay and hTERT promoter mutation assay, are listed in Table 2 and Table 3.

TABLE 2

Sequence and locations of CTNNB1 oligonucleotides used in this study

| Primer and probe name | Nucleotide location | Sequence |
|---|---|---|
| CTNNB1_F32A (SEQ ID NO: 1) | 27068-27085 | 5'-GCAGCAACAGTCTTACCT-3' |
| CTNNB1_R37A (SEQ ID NO: 2) | 27105-27120 | 5'-ctgtgtgctcttcgtgtgtggtgtCTGTGGTAGTGGCACC-3' |
| CTNNB1_BNA32 (SEQ ID NO: 3) | 27087-27103 | 5'-G + *G* + A*C* + *T* + C*T* + *G* + *G*A + *A* + *T*C + *C* + A*T* + *T*C-3'PH |
| CTNNB1_TQ32 (SEQ ID NO: 4) | 27086-27111 | 5'[6FAM]-GGACTCTGGAATCCATTCTGGTGCCA-[BHQ1]3' |
| CTNNB1_R1 (SEQ ID NO: 5) | 27201-27219 | 5'-GAGTGAAGGACTGAGAAAA-3' |
| CTNNB1_F (SEQ ID NO: 6) | 27007-27024 | 5'-CTGATTTGATGGAGTTGG-3' |
| CTNNB1_F1_AMP (SEQ ID NO: 7) | 27068-27085 | 5'-tcgtcggcagcgtcagatgtgtataagagacagGCAGCAACA GTCTTACCT-3' 5'-gtctcgtgggctcggagatgtgtataagagacagCTGTGTGCTC |
| CTNNB1_R37A_AMP_tag (SEQ ID NO: 8) | NA | TTCGTGTGTGGTGT-3' |
| CTNNB1_F2_AMP (SEQ ID NO: 9) | NA | 5'-TCGTCGGCAGCGTC-3' |
| CTNNB1_R2_AMP (SEQ ID NO: 10) | NA | 5'-GTCTCGTGGGCTCGGA-3' |

CTNNB1 is GenBank No. AY463360. The nucleotides boldfaced, having a "+", and italicized nucleotides denote BNA bases. The lower-case bases indicate a non-complementary accessory tag. The underlined bases indicate the sequencing primers. The fluorescent tags are indicated by brackets [ ] FAM, fluorescein; BBQ, BlackBerry Quencher. PH indicates a phosphorylation modification.

TABLE 3

Sequence and locations of hTERT oligonucleotides used in this study

| Primer and probe name | Nucleotide location | Sequence |
|---|---|---|
| TERT_124F1_AMP (SEQ ID NO: 11) | 43928-43945 | 5'-tcgtcggcagcgtcagatgtgtataagagacagAGGGGCTGG GAGGGCCCG-3' |
| TERT_124R1 (SEQ ID NO: 12) | 43960-43977 | 5'-GACCCCTCCCGGGTCCCC-3' |
| TERT_BNA (SEQ ID NO: 13) | 43943-43953 | 5'-g + *C*C + *C* + *C* + *C* + *T* + *C*C + *G*G-3'PH |
| TERT_R1 (SEQ ID NO: 14) | 43965-43980 | 5'-CCGACCCCTCCCGGG-3' |
| TERT_TQ1_WT (SEQ ID NO: 15) | 43944-43962 | 5'[6FAM]-CGGAGGGGCTGGGCCGG-[BHQ1]3' |
| TERT_TQ1_124 (SEQ ID NO: 16) | 43944-43962 | 5'[6FAM]-CGGAAGGGGCTGGGCCGG-[BHQ1]3' | hTERT is GenBank No. NG009265. The nucleotides boldfaced, having a "+", and italicized nucleotides denote BNA bases. The lower-case bases indicate a non-complementary accessory tag. The underlined bases indicate the sequencing primers. The fluorescent tags are indicated by brackets [ ] FAM, fluorescein; BBQ, BlackBerry Quencher. PH indicates a phosphorylation modification.

Embodiment 1: CTNNB1 Hotspot Mutation Assay

Development of a qPCR Assay for CTNNB1 Hotspot Mutations.

Figure 2A:
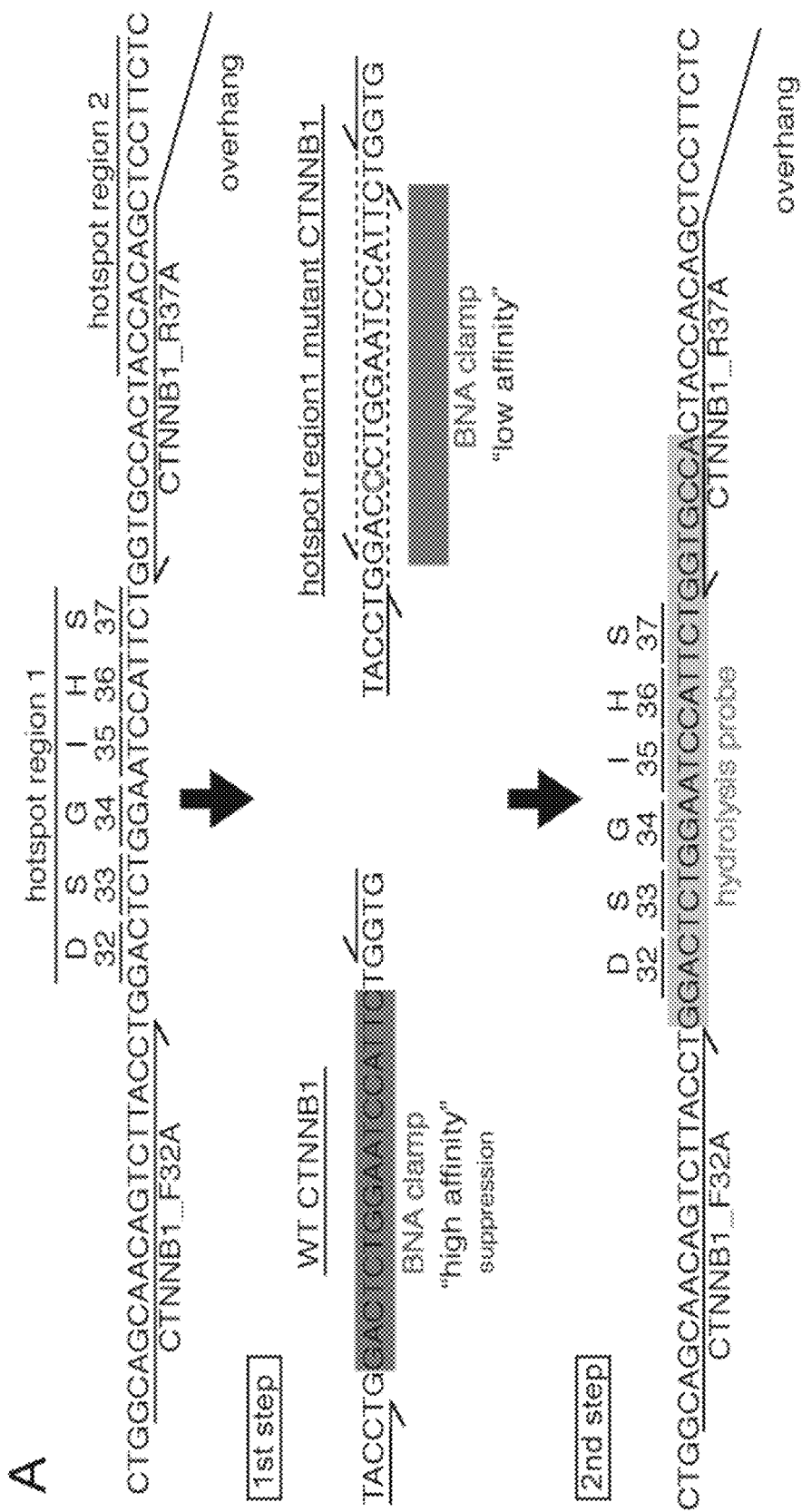
FIGS. 2A-2B show the development of a BNA-clamp mediated PCR assay to detect CTNNB1 hotspot mutations.

The CTNNB1 mutation hotspot region 1 assay was developed using a two-step BNA clamp-mediated PCR assay, illustrated in FIG. 2A. In this assay, primers were designed flanking the hotspot region 1 in the presence of a BNA clamp that targets this hotspot region (step 1). The amplified product from step 1 was then analyzed by qPCR with a hydrolysis probe that targets hotspot region 1 (step 2).

Specifically, the hotspot region of CTNNB1 (codons 32-37) was targeted with a BNA clamp just outside of this region. The first PCR reaction was performed in a thermocycler (Eppendorf, Hamburg, Germany) using the primers SEQ ID NO: 1 and SEQ ID NO: 2 (0.5 µM), BNA clamp SEQ ID NO: 3 (2 µM), dNTP (200 µM), and HotStar Taq Plus polymerase (Qiagen) under the following conditions: 95° C. for 5 minutes to activate the polymerase, then 95° C. for 30 seconds, 70° C. for 20 seconds, and 60° C. for 30 seconds cycled 15 times, followed by 72° C. for 4 minutes.

Amplified DNA from the first PCR step was next quantified by a real-time PCR step. The DNA template (1 µl) was added to a mixture containing the primer set SEQ ID NO: 1 and SEQ ID NO: 2 (1 µM), a hydrolysis probe (SEQ ID NO: 4; 0.2 µM), and 1× LightCycler® Probes Master (Roche). The qPCR was carried out using a LightCycler® 480 real-time PCR system under the following conditions: 95° C. for 5 minutes to activate the polymerase, then 95° C. for 10 seconds, 60° C. for 10 seconds, and 72° C. for 10 seconds cycled 40 times.

Determining the Sensitivity of the CTNNB1 Hotspot Mutation Assay

Figure 2B:
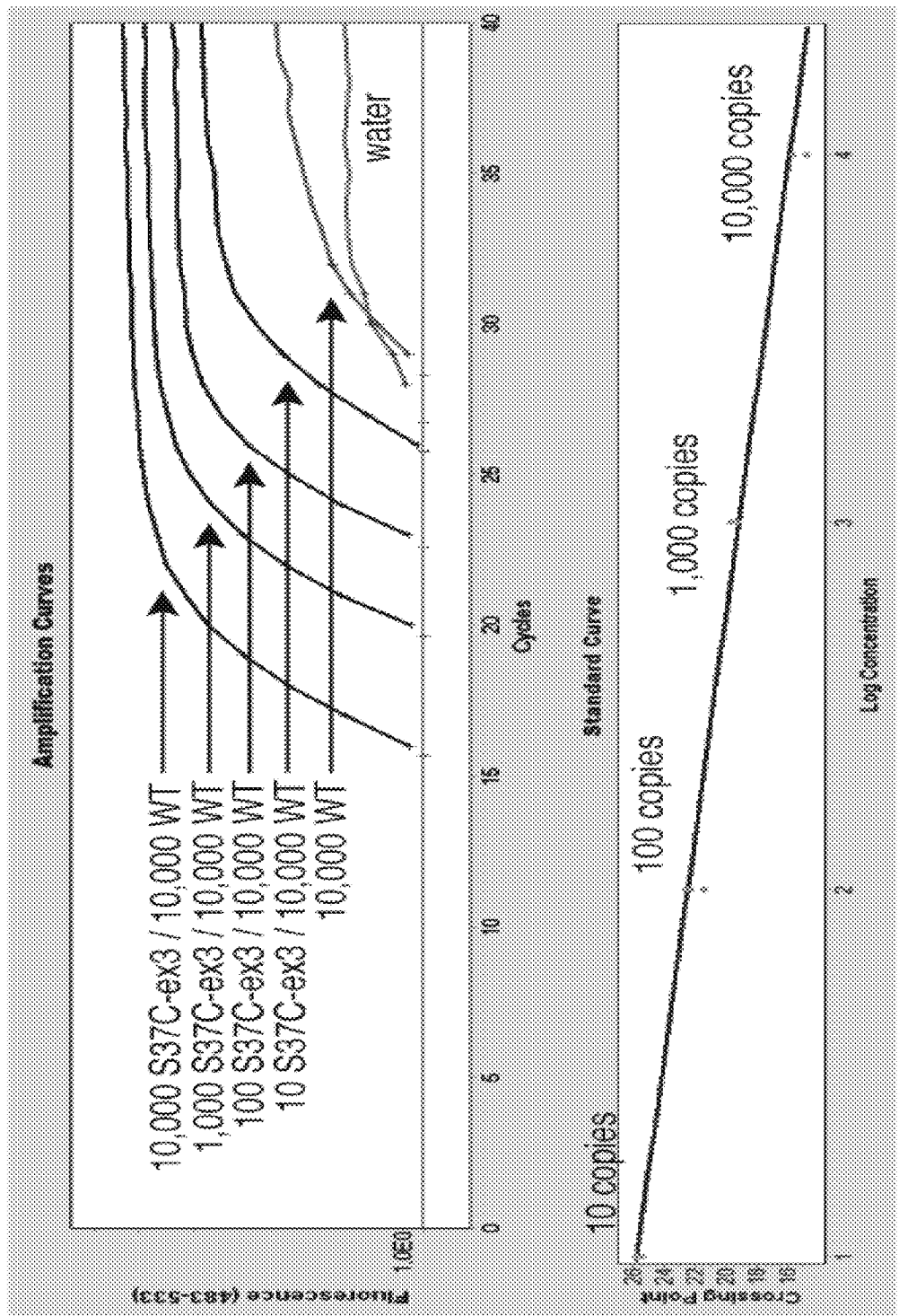

FIG. 2B shows amplification curves of the standards in the BNA clamp mediated CTNNB1 assay. Curves were generated with varying dilutions of the S37C-ex3 plasmid in reconstituted standards of sonicated Hep3B cell line DNA. Analysis was carried out using Roche LightCycler® 480 software. Specifically, to determine quantification values and sensitivity, serial dilutions of a plasmid containing the CTNNB1 gene with TCT to TGT mutation at codon 37 (37Cys3) were used ranging from 10-10,000 copies. Sonicated Hep3B DNA (10,000 copies) and HuG DNA (10,000 copies) were used as negative controls.

Sequencing of Samples to Validate qPCR Results

Figure 2C:
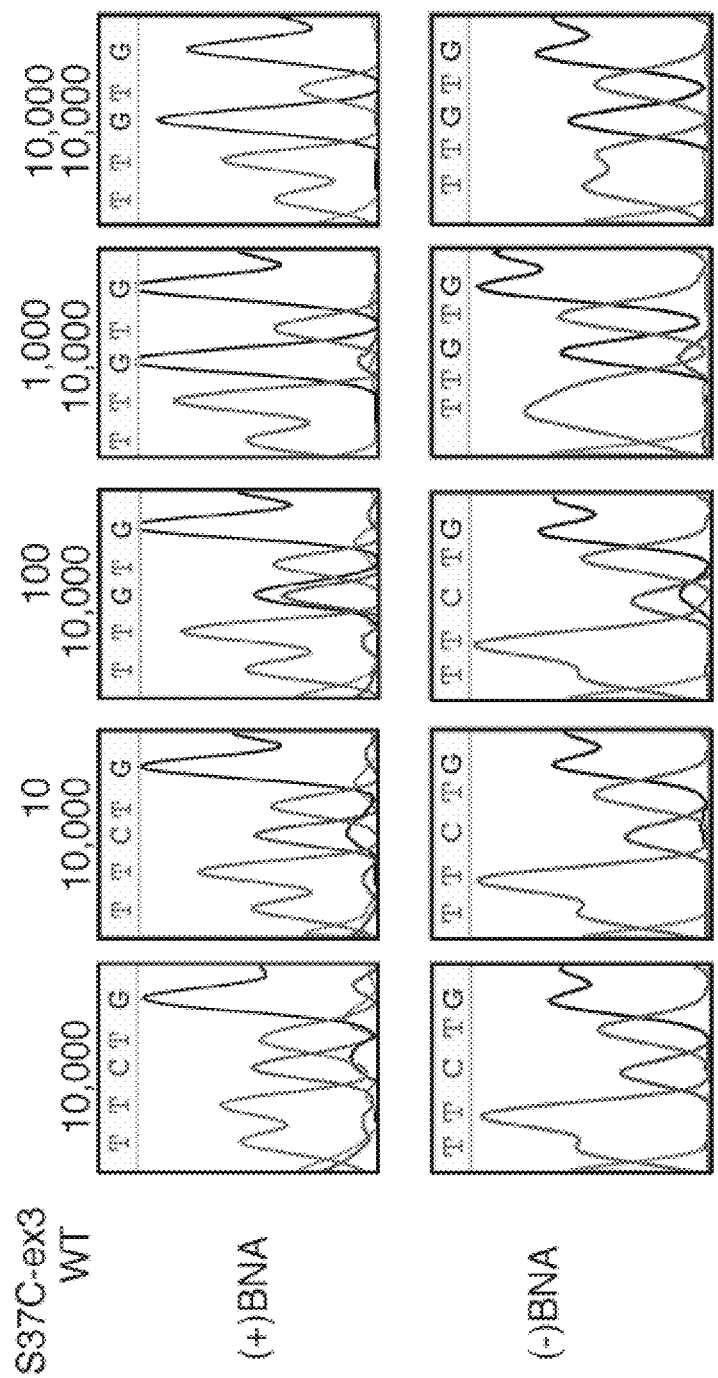
FIG. 2(C) shows Sanger sequencing of the dilutions of the pCTNNB1_S37C plasmid in a background of wild-type sonicated Hep3B cell line DNA.

As shown in FIG. 2C, dilutions of the S37C-ex3 plasmid in reconstituted WT standards was sequenced to contrast the improved sensitivity when BNA is present. Specifically, isolated tissue DNA (1 ng) was amplified in a PCR reaction using the B-Cat F (5'-ctgatttgatggagttgg-3') and B-CAT R1 (5'-gagtgaaggactgagaaaa-3') primer set (0.5 µM), dNTP's (200 µM), and HotStar Taq Plus polymerase (Qiagen) in PCR buffer under the following conditions: 95° C. for 5 minutes to activate the polymerase, then 95° C. for 30 seconds, 52-56° C. for 30 seconds, and 72° C. for 30 seconds cycled 40 times, followed by 72° C. for 4 minutes. For sequencing using the BNA clamp, isolated tissue DNA (2 ng) was amplified in a PCR reaction using the B-Cat F32A and R37A primer set (0.5 µM), B-Cat BNA, dNTP's, and HotStar Taq Plus polymerase (Qiagen) in PCR buffer under the following conditions: 95° C. for 5 minutes to activate the polymerase, then 95° C. for 30 seconds, 70° C. for 20 seconds, and 60° C. for 30 seconds cycled 25 times, followed by 72° C. for 4 minutes. Next, a second PCR reaction was carried out using the B-Cat F1_AMP and R37_AMP_tag primer set (0.2 µM), dNTP's (200 µM), and HotStar Taq Plus polymerase (Qiagen) in PCR buffer under the following conditions: 95° C. for 5 minutes to activate the polymerase, then 95° C. for 30 seconds, 60° C. for 30 seconds, and 72° C. for 30 seconds cycled 5 times, then 95° C. for 30 seconds, and 70° C. for 30 seconds cycled 5 times, followed by 72° C. for 4 minutes.

All preparations were cleaned using a Zymo DNA (PCR) Clean-up and Concentration kit (Zymo Research) according to the manufacturers instructions, and verified for correct size using a Lonza gel. All samples were dried in a speed-vac and submitted to the NAPCore Facility (CHOP, Philadelphia, Pa.) for sequencing.

Figure 3A:
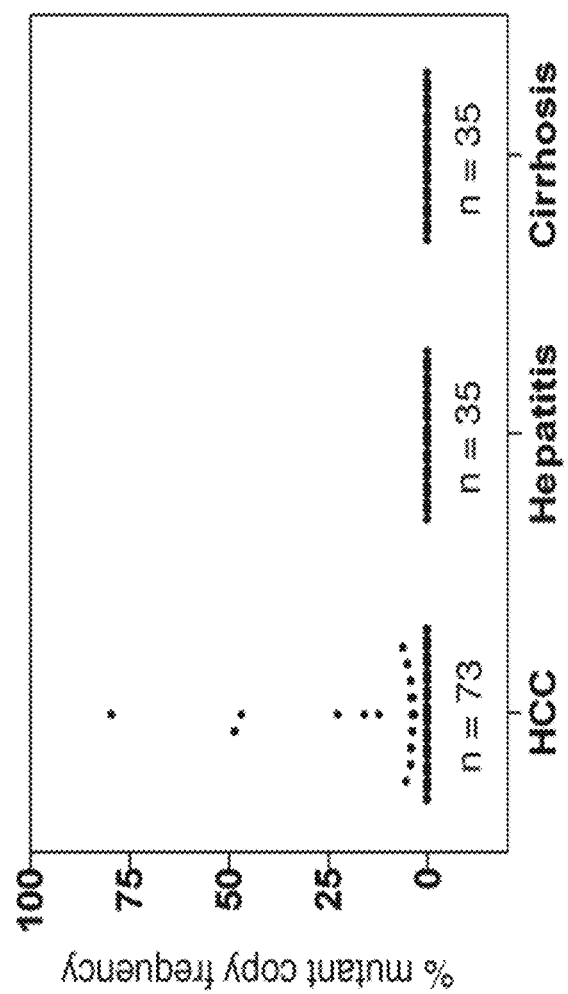

The CTNNB1 Hotspot Mutation Assay Discriminates Between HCC and Non-HCC Diseased Tissue The qPCR CTNNB1 assay was used to test tissue biopsies of patients with HCC, hepatitis, and cirrhosis. As shown in FIG. 3A, with the HCC subset (n=73) 18 patients tested positive to varying degrees above the human genomic DNA standard, while none of hepatitis (n=35) or cirrhosis (n=35) samples tested positive. Next, a selection of the HCC population was further analyzed by Sanger sequencing to confirm the mutation in hotspot region 1. As shown in FIG. 3B, of the 23 negative samples that were selected, none contained a mutation after sequencing analysis. For one of these patients (A47K), we identified a mutation in the CTNNB1 hotspot region 2, which was not detected since the designed BNA clamp only targets hotspot region 1. For the samples that were identified as positive by the qPCR assay, 11 were analyzed by Sanger sequencing for validation. 4 of the 11 samples were confirmed by Sanger sequencing, and these mostly correlated with higher mutant copy number with the exception of A53K, which detected low but was clearly mutated from the sequencing results. Addition of BNA to the amplification reaction improved detection, allowing three additional samples to be confirmed.

Figure 4A:
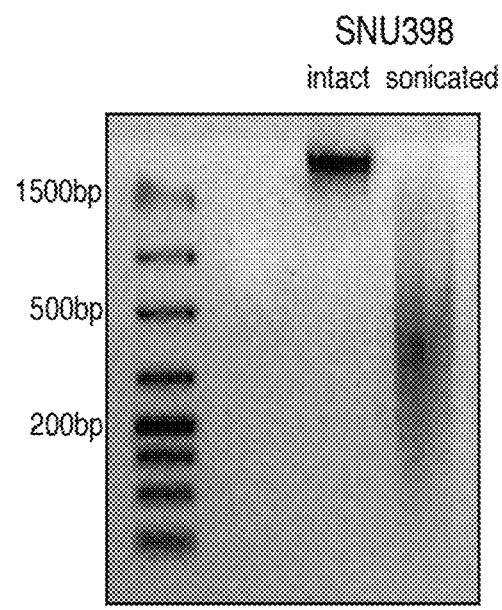
FIGS. 4A-4B show the standardization of the CTNNB1 assay using SNU398 genomic DNA.
Figure 4B:
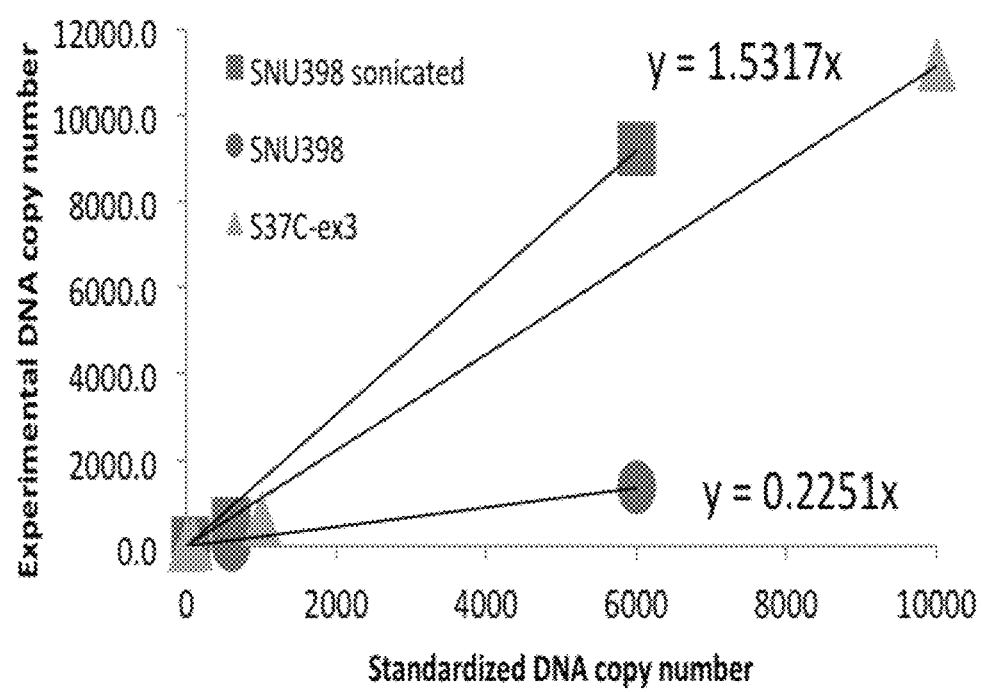

FIG. 4 shows the standardization of the CTNNB1 assay using SNU398 genomic DNA. The smaller size of a plasmid (3-5 Kb) such as pCTNNB1_S37C becomes an easier target for PCR amplification compared the same mutation in human genomic DNA (3,000 Mb). As shown in FIG. 4A, to highlight this phenomenon we took a portion of an SNU398 stock and fragmented it through sonication, giving rise to 200-500 bp genomic fragments. As shown in FIG. 4B, compared side by side, the sonicated cell line was 7-times overestimated of the intact genomic DNA. In addition, the SNU398 cell line is heterozygous for the S37C mutation, meaning these observations are 2-times underestimated when compared to the plasmid control. This means that sonicated genomic DNA is approximately 3-times overestimated, and intact genomic DNA is approximately 2.2-times underestimated.

Figure 5:
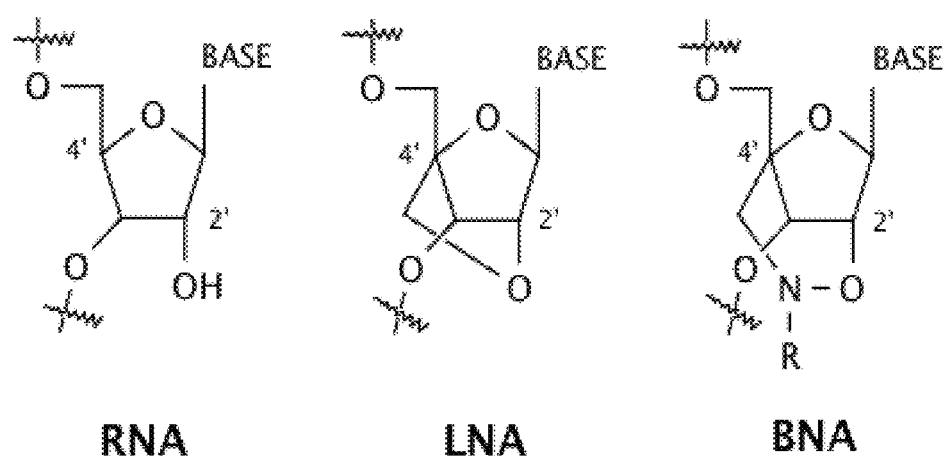
FIG. 5 is a chemical structure drawing illustrating unmodified RNA, locked nucleic acid (LNA), and bridged nucleic-acid (BNA).

FIG. 5 is a chemical structure drawing illustrating unmodified RNA, locked nucleic acid (LNA), and bridged nucleic-acid (BNA). In LNA the bridge is a 2'-O-4'-methylene bridge, and in BNA the bridge is a 2'-O-4'-aminoethylene bridge.

Detection of CTNNB1 Hotspot Mutations from cfDNA in the Urine Originates from the HCC Tumor Total urine DNA from 13 patients was isolated, fractionated into LMW DNA, and quantified by qPCR for CTNNB1 hotspot mutation as described above. From our studies of analyzing CTNNB1 mutation in patients diagnosed with HCC, we identified a subset of 13 patients that presented as positive with this assay (Table 4). This indicated that the assay was applicable to the short, low abundant DNA found in urine. While tissue contains localized DNA from an identified tumor, urine is a source of heterogeneous DNA fragments. In order to show that the DNA we detected in urine as positive for CTNNB1 mutation came from the tumor in the liver, we followed these patients after liver cancer resection. Urine was tested within a day of surgery, and then again after surgery at a follow-up visit. In 7 of these patients, we could no longer detect CTNNB1 mutation after surgical removal of the tumor, including patient UA61 that had the highest mutant copy detection. The other 6 patients remained positive for CTNNB1 mutation after surgery, and all 6 had recurrence of HCC within 5 years. Interestingly, one patient tested very high for CTNNB1 mutation after surgery, and was diagnosed with lung metastasis nearly a year post-surgery. Only 4 patients (or 31%) were free of recurrence in this study, and all 4 were also free of CTNNB1 mutation after surgery. Collectively, this data provides supportive evidence that CTNNB1 mutations identified from urine cfDNA is derived from the liver tumor of HCC patients.

TABLE 4

Detection of CTNNB1 hotspot mutation from urine of HCC patients before & after tumor resection

| Sample ID | Serum AFP (ng/mL) | CTNNB1 qPCR (copies/ml) Before treatment | CTNNB1 qPCR (copies/ml) After treatment | Months post treatment | Recurrence Detected | Months post treatment | Method |
|---|---|---|---|---|---|---|---|
| UA55 | 6.88 | 2-20 | ND | 10 | No | — | — |
| UB68 | 4.99 | 2-20 | 29 | — | Yes | 26 | RFA |
| UB81 | 19.09 | 2-20 | 881 | — | Lung | 13 | CT |
| UB83 | 1.81 | 2-20 | 23 | — | Yes | 51 | MRI |
| UB84 | 11.73 | 2-20 | 2-20 | — | Yes | 21 | MRI |
| UB53 | 6.45 | 21 | ND | 2 | No | — | — |
| UA01 | — | 24 | ND | 10 | Yes | 21 | RFA |
| UB66 | 3.8 | 29 | ND | — | No | — | — |
| UA26 | 6101 | 39 | ND | 2 | Yes | 4 | RFA |
| UA20 | 4.03 | 42 | ND | 3 | No | — | — |
| UB76 | 0 | 101 | 34 | 2 | YES | 7 | CT |
| UA60 | — | 142 | 26 | 1 | Yes | 47 | MRI |
| UA61 | 4.28 | 498 | ND | 1 | Yes | 57 | MRI |

ND: not detectable or blow limit of detection

Embodiment 2: hTERT Promoter Mutation Assay

Development of a qPCR Assay for hTERT Promoter Mutations

Figure 6A:
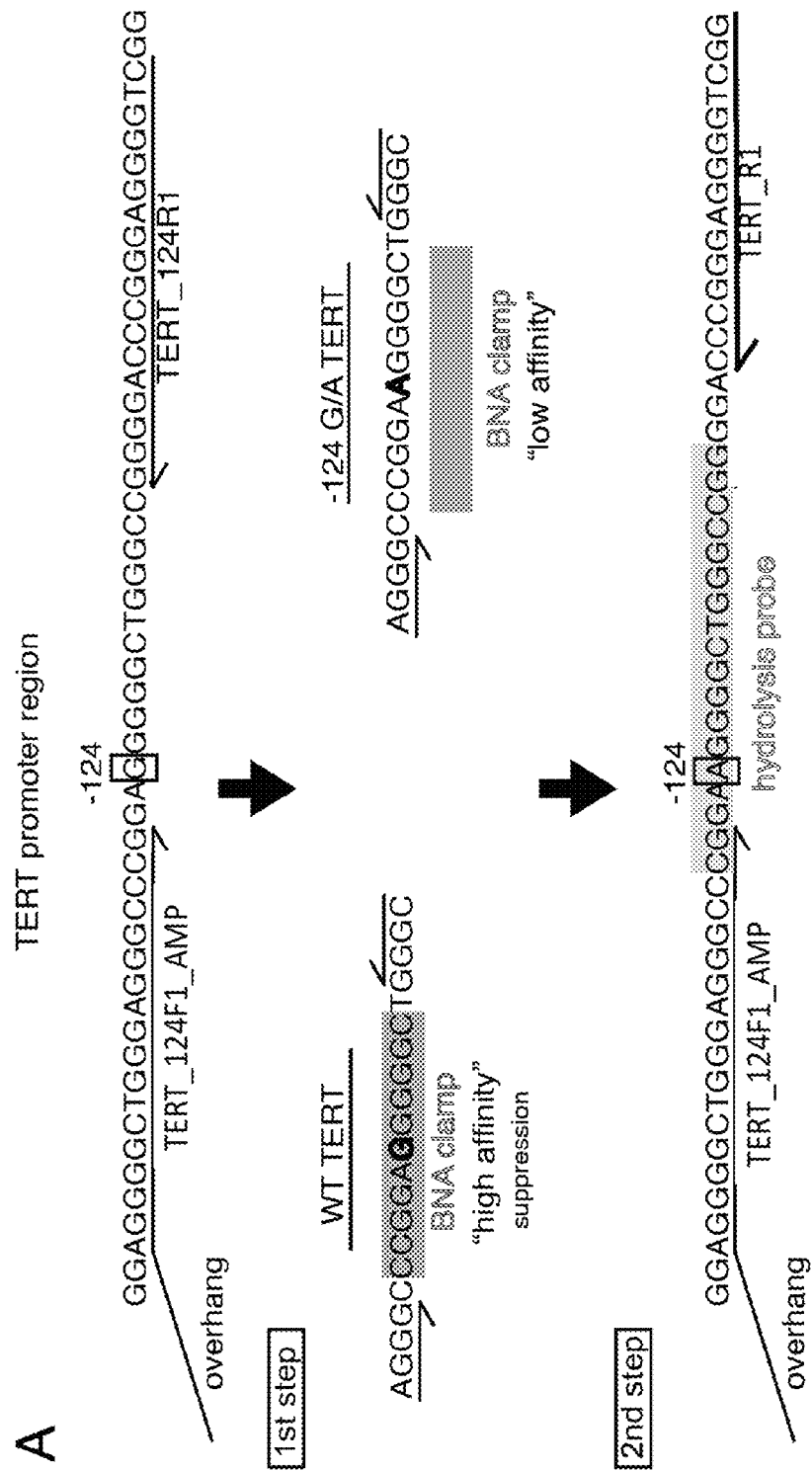
FIGS. 6A-6B provide a schematic of a BNA-clamp mediated PCR assay to detect hTERT mutations.

The hTERT promoter mutation quantification assay was developed using a two-step BNA clamp-mediated PCR assay. The schematic of the assay is illustrated in FIG. 6A. Primers were designed flanking the hotspot region 1 in the presence of a BNA clamp that targets this hotspot region (step 1). The amplified product from step 1 was then analyzed by qPCR with a hydrolysis probe that targets the −124 G/A mutation (step 2). Specifically, the region −129 to −119 nt upstream of the start codon of the hTERT gene (NG_009265: 43927-43976) was targeted with a BNA clamp primer that is a perfect complementary match of non-mutated. The first PCR reaction was performed in a thermocycler (Eppendorf, Hamburg, Germany) using this primer set of SEQ ID NO: 11 and SEQ ID NO: 12 (0.25 µM), BNA clamp SEQ ID NO: 13 (1 µM), dNTP (200 µM), DMSO (5%), and HotStar Taq Plus polymerase (Qiagen) under the following conditions: 95° C. for 5 minutes to activate the polymerase, then 95° C. for 30 seconds, 78-82° C. for 20 seconds, and 70-74° C. for 45 seconds cycled 35 times, followed by 72° C. for 4 minutes. Amplified DNA from the first PCR step was next quantified by a real-time PCR step. The DNA template (1 µl) was added to a mixture containing the primer set from step 1 (1 µM), a hydrolysis probe (SEQ ID NO 16; 0.2 µM), and 1× LightCycler® Probes Master (Roche). The qPCR was carried out using a LightCycler® 480 real-time PCR system under the following conditions: 95° C. for 5 minutes to activate the polymerase, then 95° C. for 10 seconds, 61° C. for 10 seconds, and 72° C. for 10 seconds cycled 40 times.

Determining the Sensitivity of the hTERT Promoter Mutation Assay

Figure 6B:
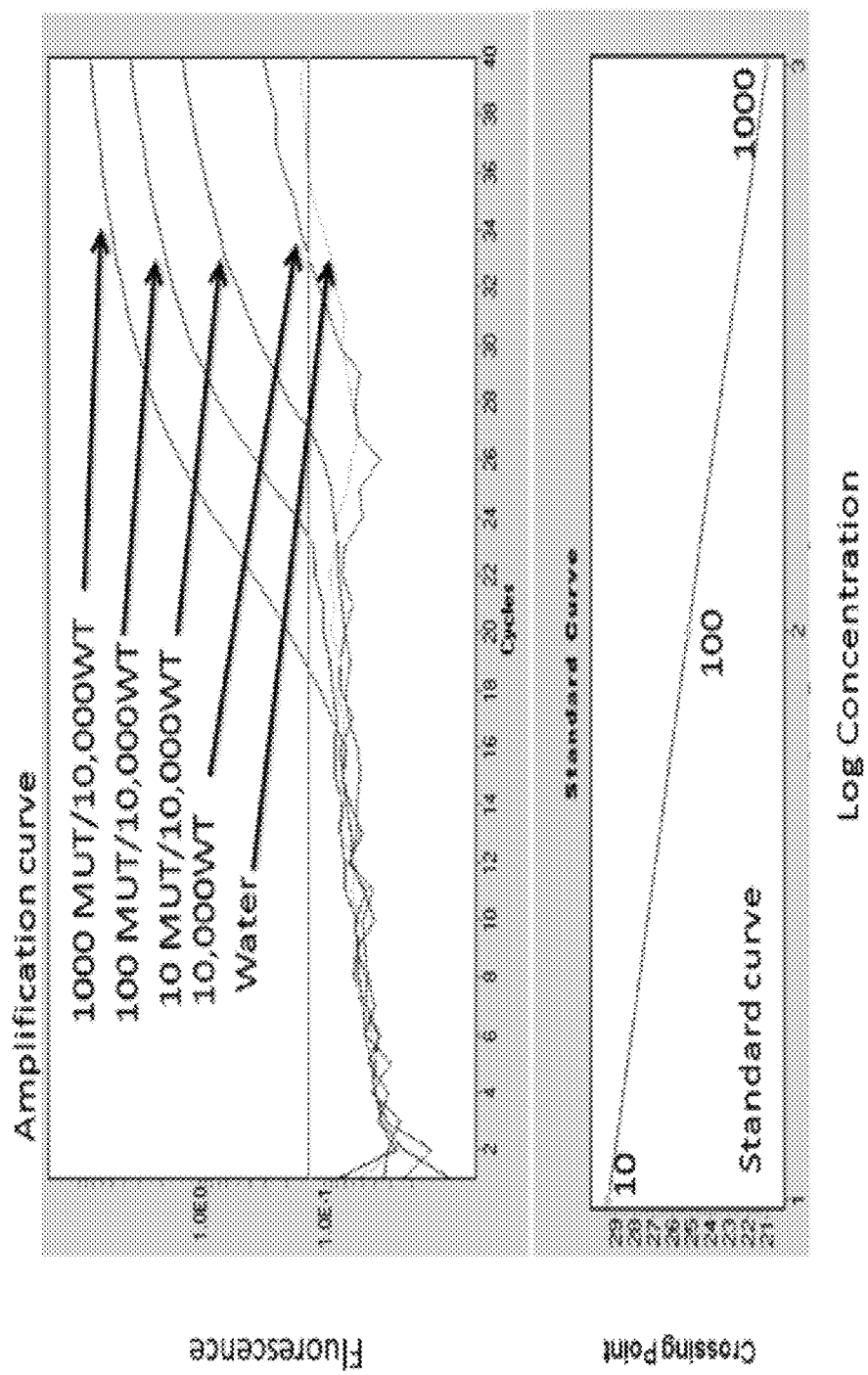
Figure 7A:
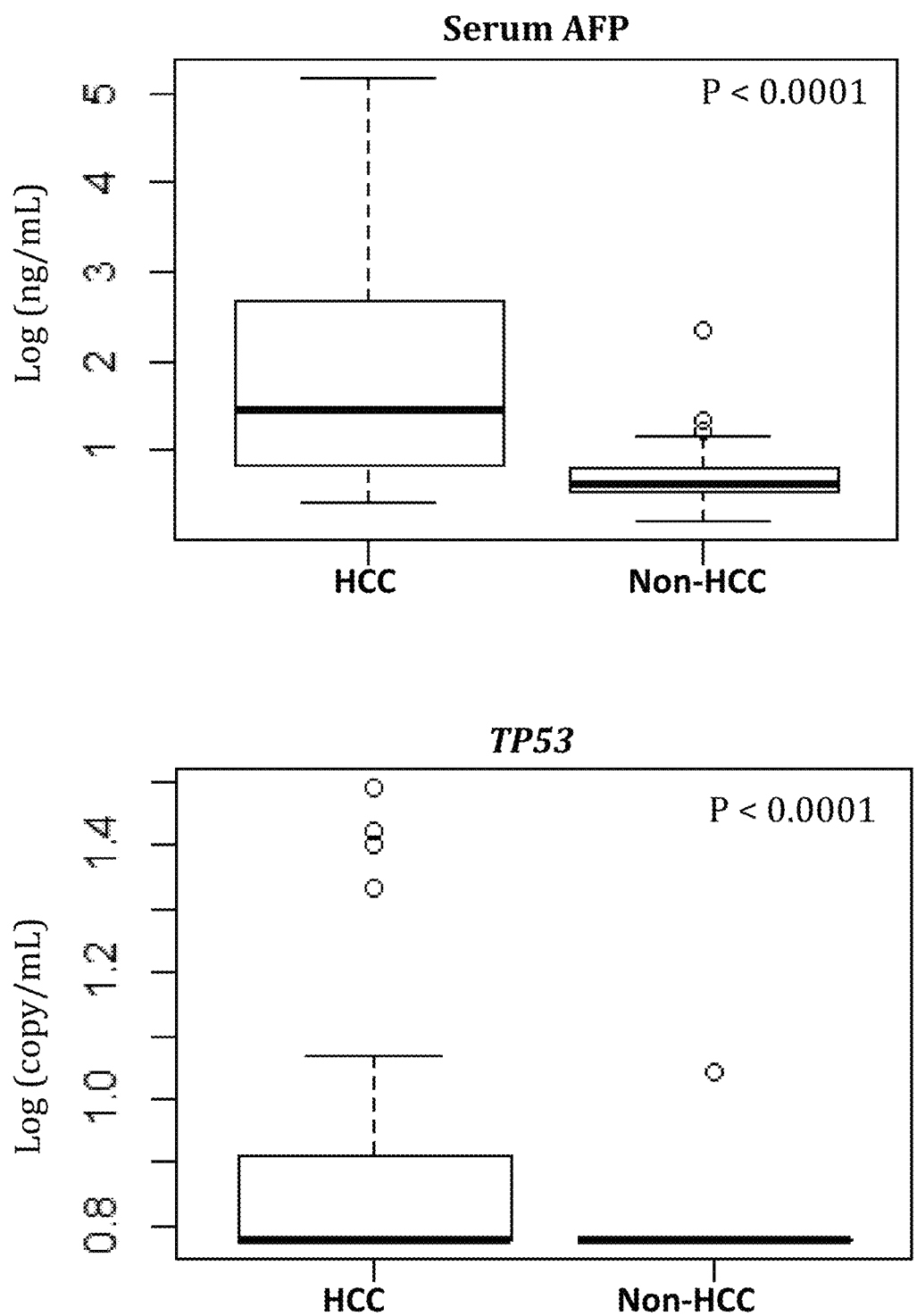
FIGS. 7A-7F provide box plots showing five urine DNA biomarkers (mRASSF1A, mGSTP1, TP53, CTNNB1 and hTERT), along with serum AFP, in distinguishing HCC from non-HCC: Box plot 7(A) shows serum AFP (top) and TP53 249T (bottom), 7(B) shows mRASSF1A (top) and mGSTP1 (bottom), 7(C) shows CTNNB1 (top) and hTERT (bottom) hotspot mutations.
Figure 7B:
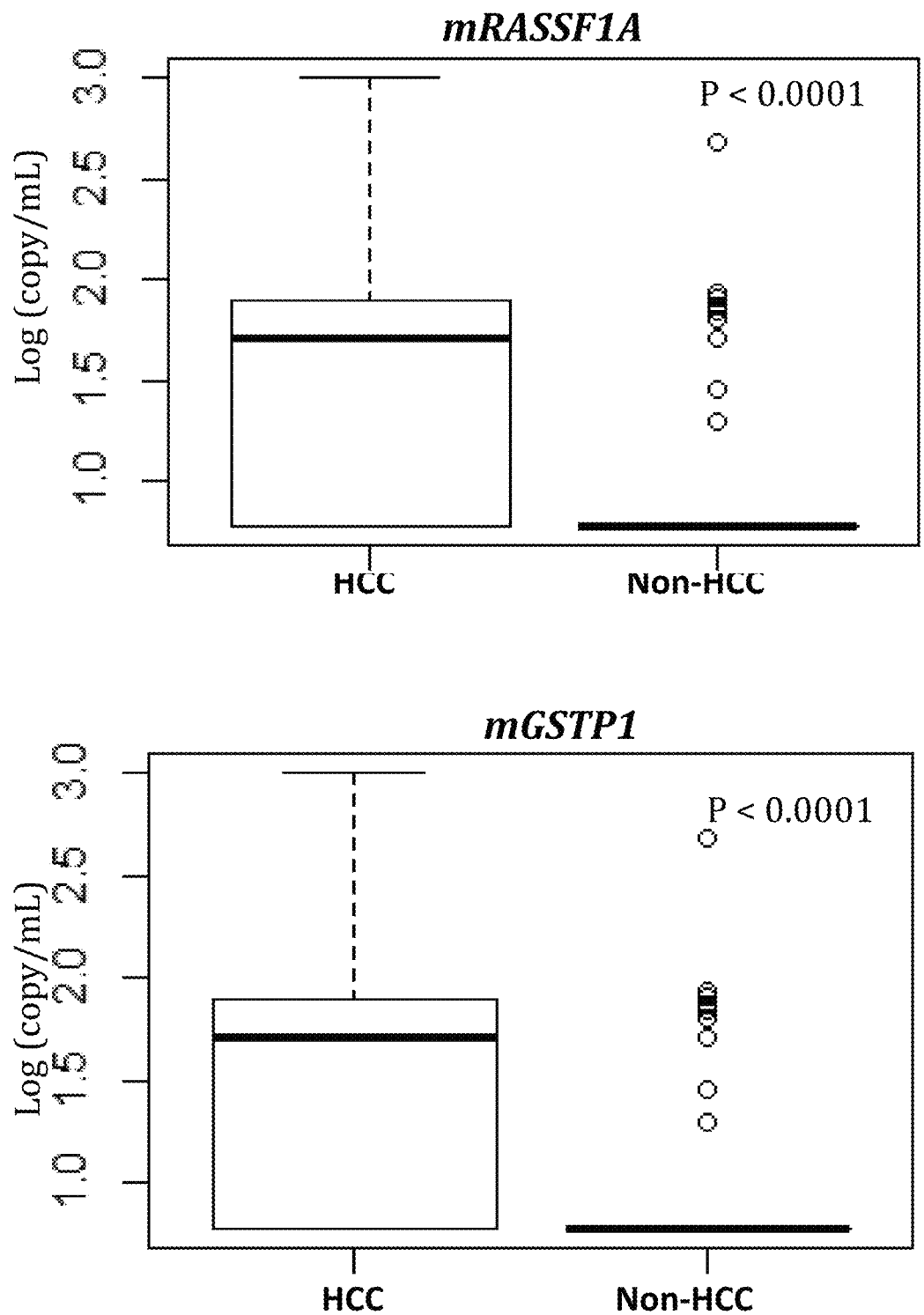
Figure 7C:
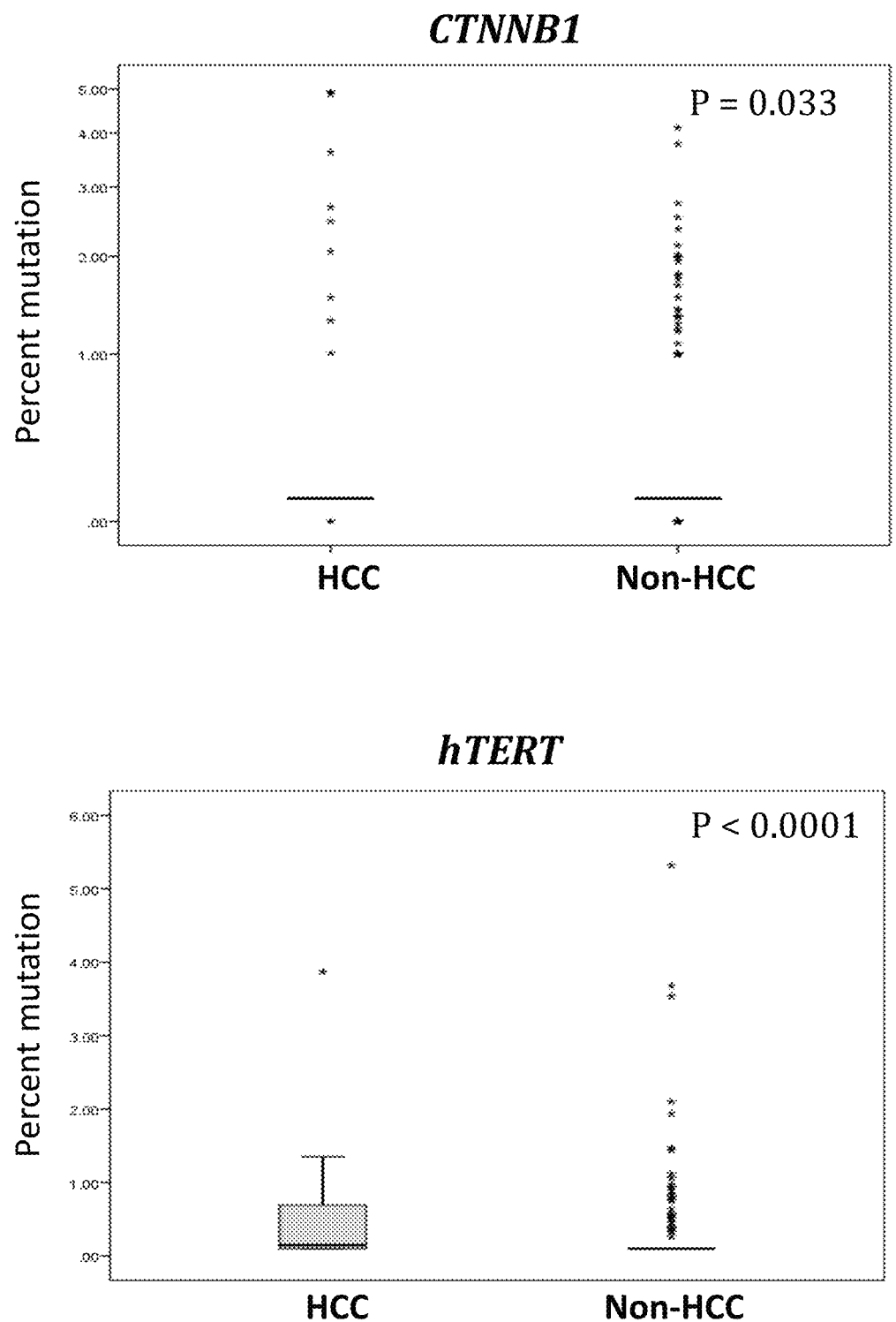
Figure 7D:
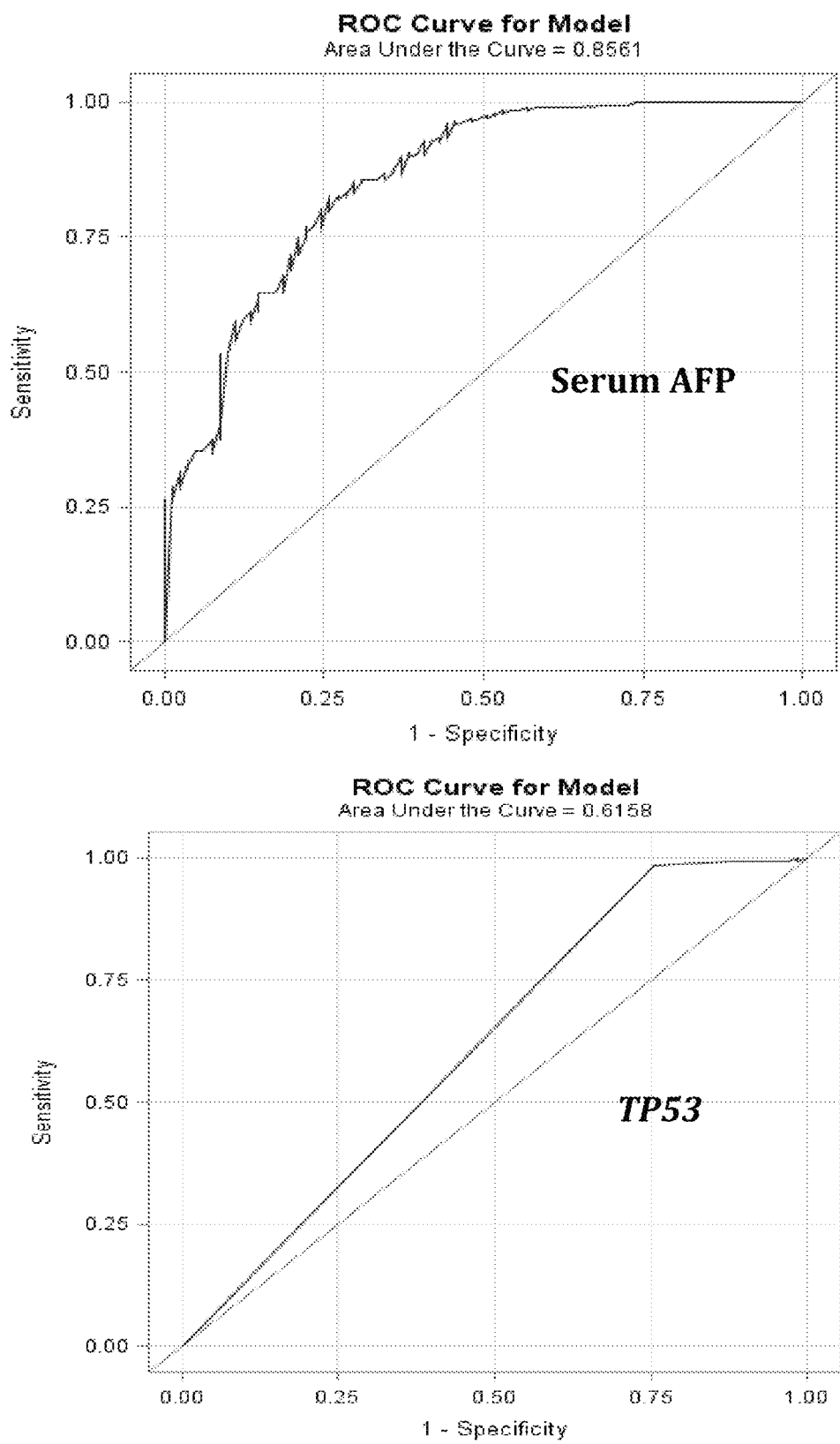
Figure 7E:
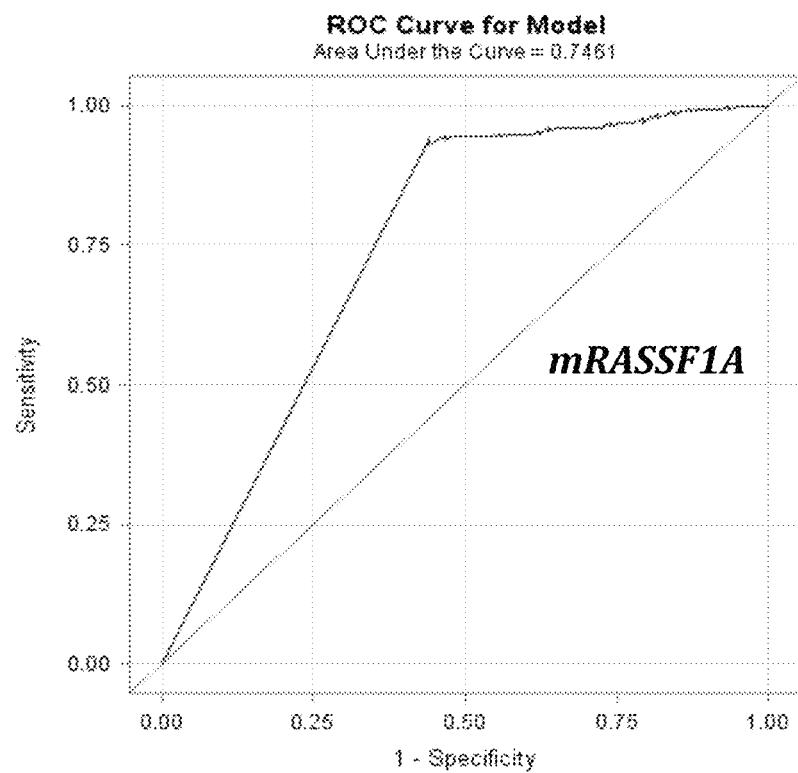
Figure 7E:
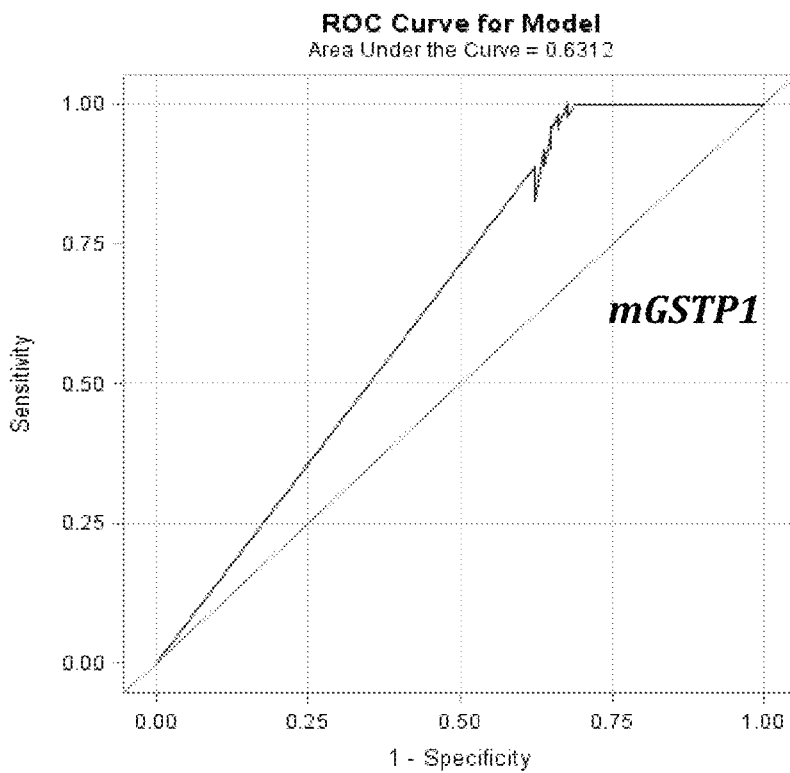
Figure 7F:
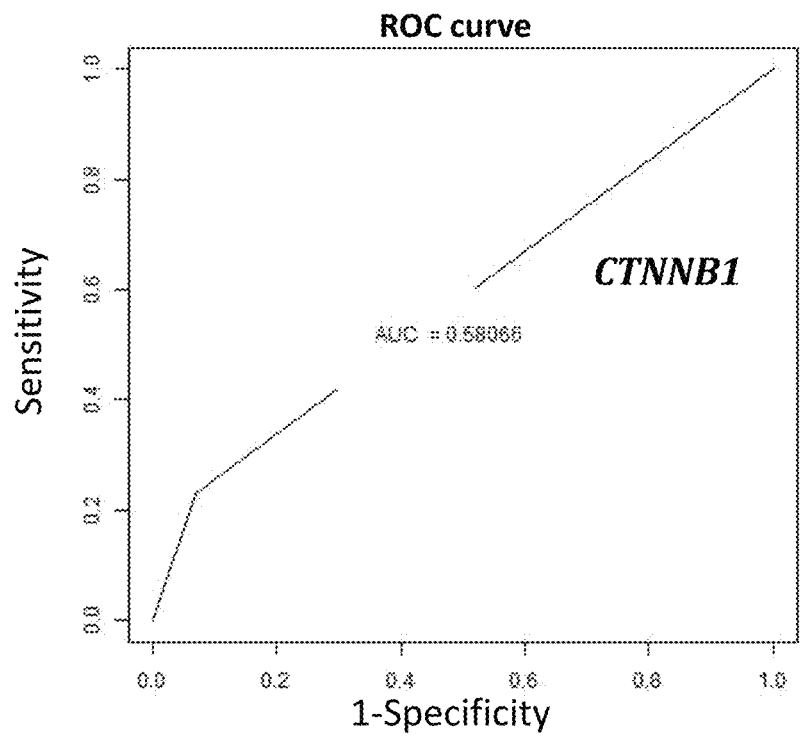
Figure 7F:
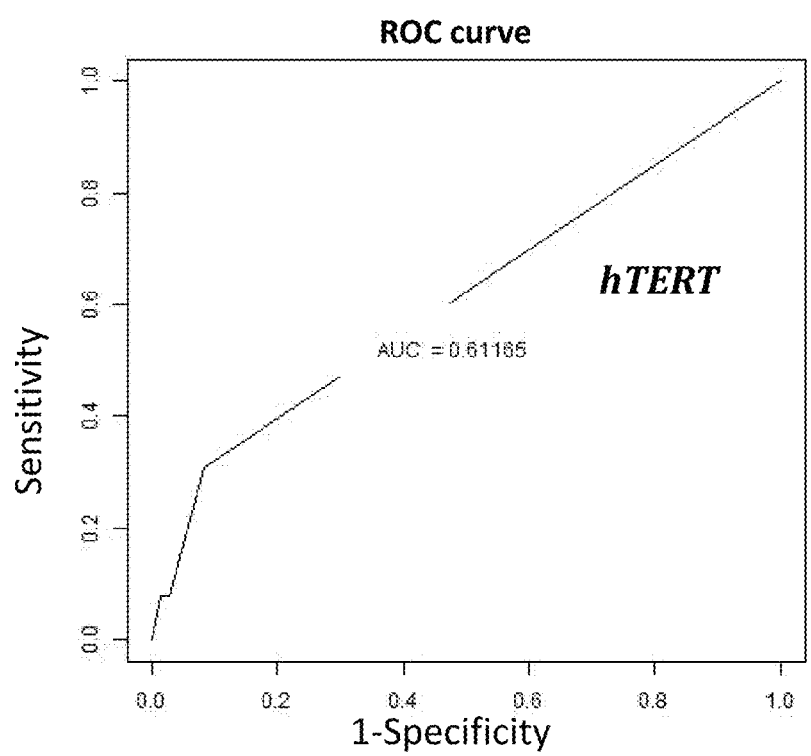

FIG. 6B illustrates amplification curves of the standards in the BNA clamp mediated hTERT mutation assay. Curves were generated with varying dilutions of the sonicated SNU398 cell line (known −124 G/A mutation) in reconstituted sonicated Hep3B cell line. Specifically, serial dilutions of sonicated SNU398 cell line DNA (harboring the hTERT promoter mutation) were used ranging from 10-1,000 copies in order to determine quantification values and sensitivity. Sonicated Hep3B cell line DNA (10,000 copies) and was used as a negative control. Analysis was carried out using Roche LightCycler® 480 software.

The hTERT Promoter Mutation Assay Discriminates Between HCC and Non-HCC Diseased Tissue Of 72 HCC tissue samples tested, 26 were found to harbor a G/A −124 promoter mutation in the hTERT gene as determined by Sanger sequencing (Table 5). These samples were all tested with the hTERT-124 promoter mutation assay. Out of the 26 samples with a known G/A −124 mutation, 21 were detected by the assay. For the 46 samples without a G/A −124 mutation, 40 were found negative by the assay. The six samples that detected positive with the assay were actually found to harbor the mutation by sequencing when BNA was used to help enrich the mutant. This indicates the mutation in some tissue samples is too low for detection in tissue, however it can be picked up by the hTERT mutation assay.

TABLE 5 hTERT promoter mutant analysis from HCC tissue

| Sanger | | qPCR | |
|---|---|---|---|
| − | 46 | − | 40 |
| | | + | 6 |
| + | 26 | − | 5 |
| | | + | 21 |

Embodiment 3: Evaluation of 5 DNA Biomarkers for Distinguishing HCC from Non-HCC Performance of each biomarker for distinguishing HCC from non-HCC in the study population described in Table 1.

FIG. 7 shows the (A-C) summary of box plot of biomarker values in two disease groups, HCC and non-HCC, and p-values between the biomarker values between two disease groups and (D-F) the univariate ROC for the study population described in Table 1, for distinguishing HCC (n=84) from non-HCC (97 hepatitis and 106 cirrhosis) subjects. The area under the ROC curve for each marker is shown. Box plots were generated to assess each urine biomarker in relationship with HCC status. As shown in FIG. 7A-7C, serum AFP, mRASSF1A, mGSTP1, and TP53, and hTERT had statistically significant higher levels in HCC as compared to non-HCC (Wilcoxon rank sum test P<0.0001). Next, to evaluate the performance of each marker in detecting HCC, a univariate logistic regression model was generated for each individual biomarker on the entire dataset. ROC curves were generated and AUCs were calculated, as shown in FIG. 7D-7F. In this study cohort, none of urine biomarkers performed better individually than serum AFP (AUC 0.8561), with AUC ranging from 0.51 to 0.7461.

Performance of Urine DNA Biomarker Panel for Distinguishing HCC from Non-HCC.

Figure 8:
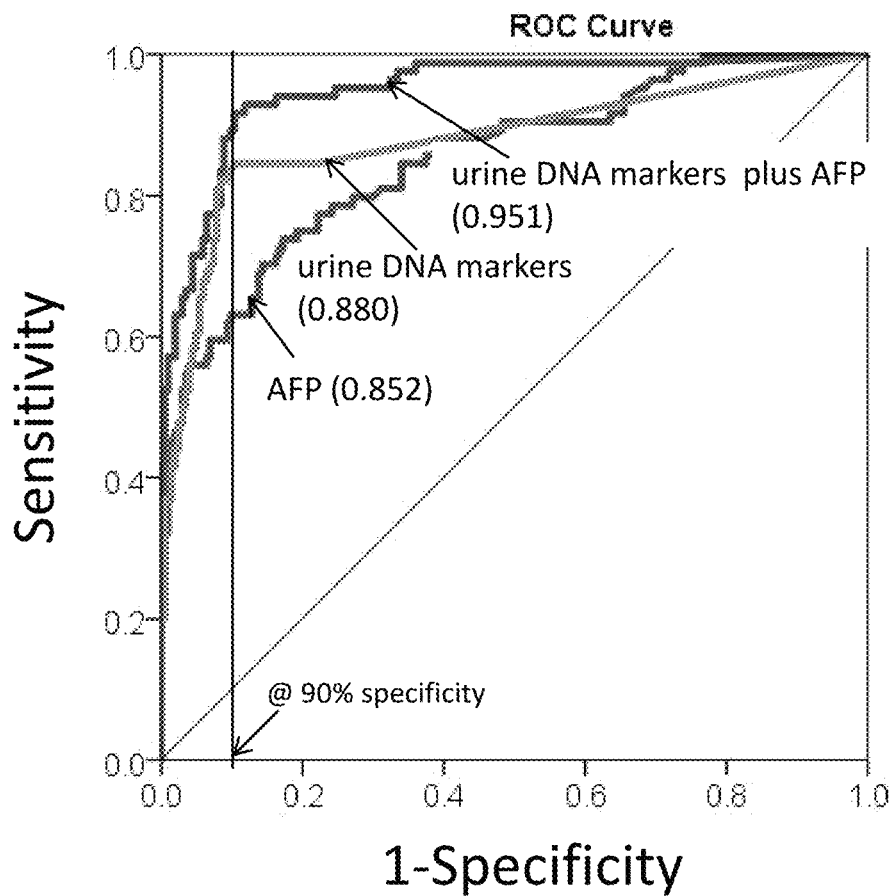
FIG. 8 shows the ROC curves generated using a multivariate statistical method of analysis using the HCC urine biomarker panel and serum AFP as variables for distinguishing HCC from non-HCC (top); The table below compares the sensitivity of serum AFP, urine DNA markers and "urine DNA markers plus AFP" at a fixed specificity of 80% and 90%.
Figure 9A:
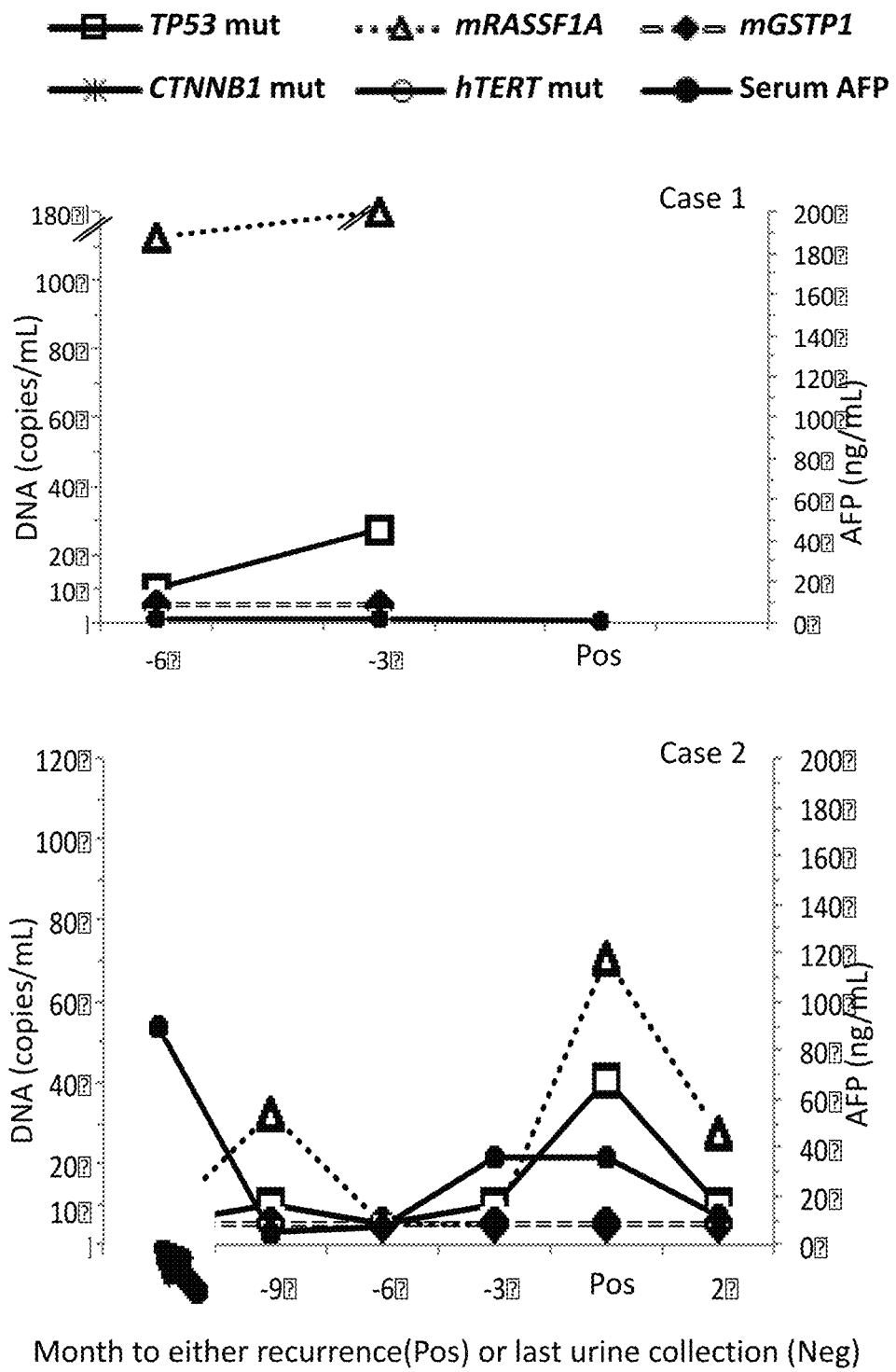
FIGS. 9A-9E illustrate DNA biomarkers levels in serial urine samples from 10 patients (Cases 1-10) monitored for HCC recurrence. Three DNA biomarker values (copies/mL urine), TP53 249T mutation (TP53mut) (open square), methylated RASSF1A (mRASSF1A) (open triange) and methylated GSTP1 (mGSTP1) (solid diamond), along with serum AFP (ng/mL serum), were plotted at office visits until the last available visit in which an MRI was performed. The "Pos" represents detection of HCC recurrence by MRI and the "Neg" represents no recurrence was detected by MRI at the time of the visit. HCC: hepatocellular carcinoma; MRI: magnetic resonance imaging; AFP: alpha fetal protein FIG. 9(A) Case 1 (top) and Case 2 (bottom), FIG. 9(B) Case 3 (top) and Case 4 (bottom), FIG. 9(C) Case 5 (top) and Case 6 (bottom), FIG. 9(D) Case 7 (top) and Case 8 (bottom), FIG. 9(E) Case 9 (top) and Case 10 (bottom).
Figure 9B:
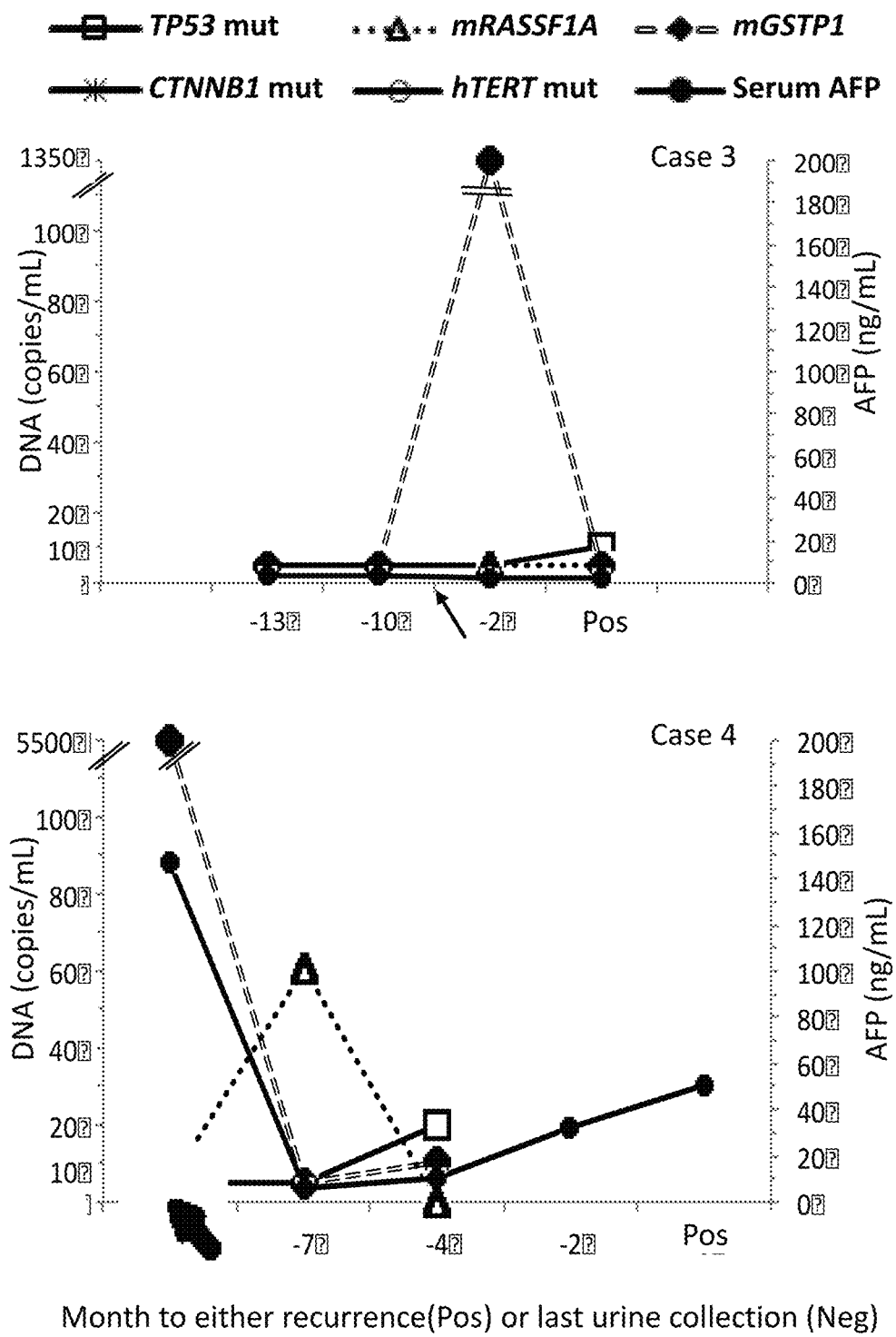
Figure 9C:
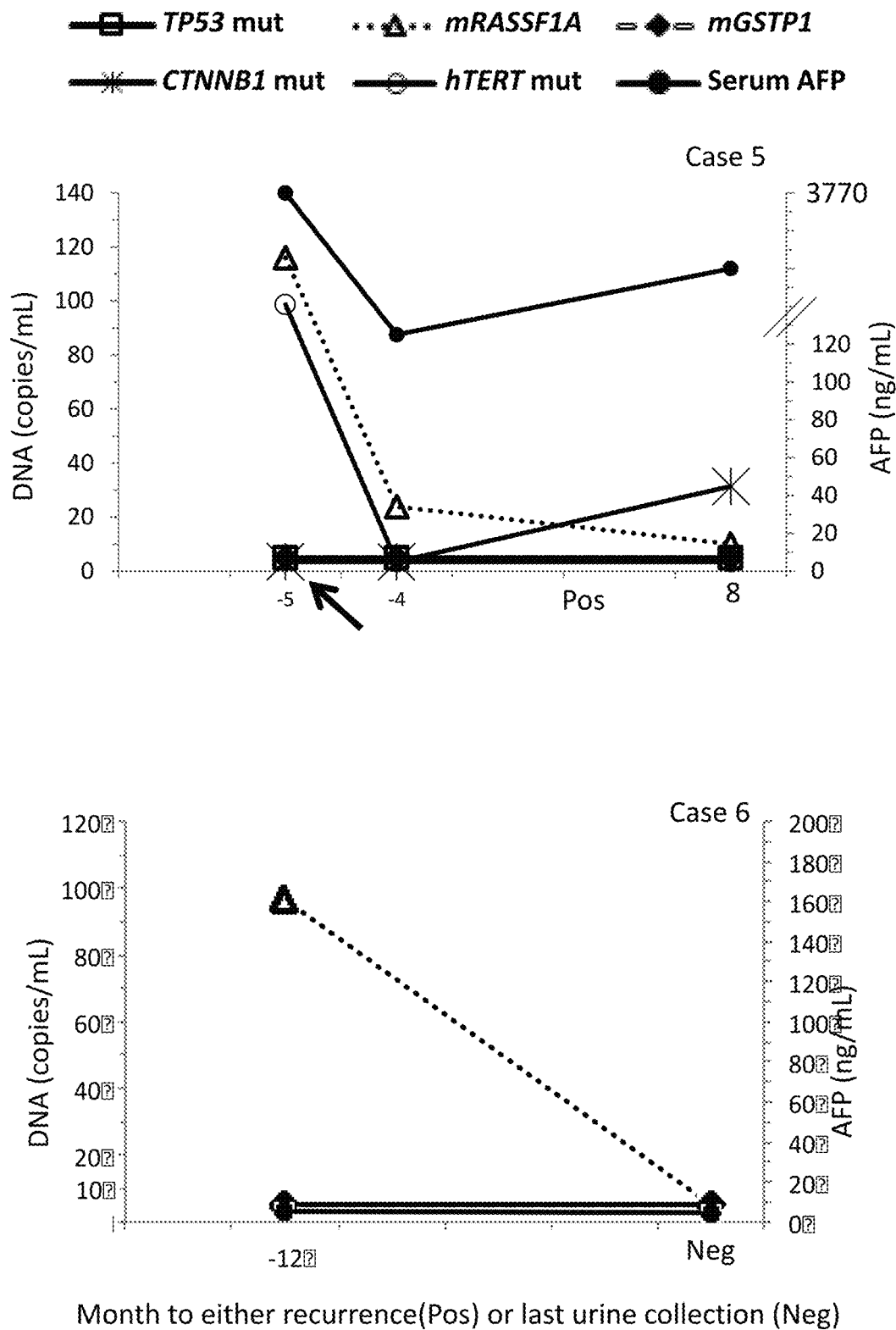
Figure 9D:
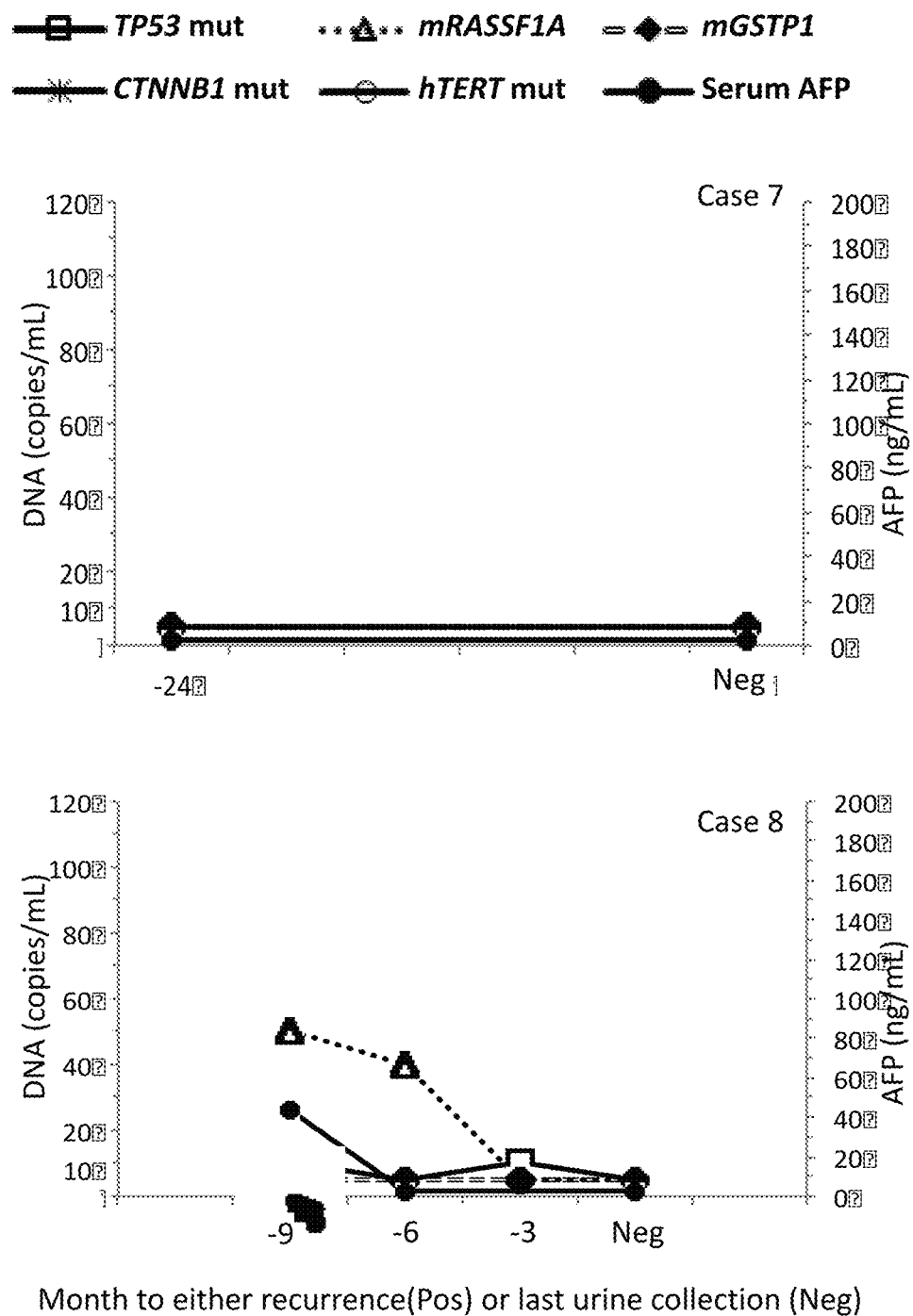
Figure 9E:
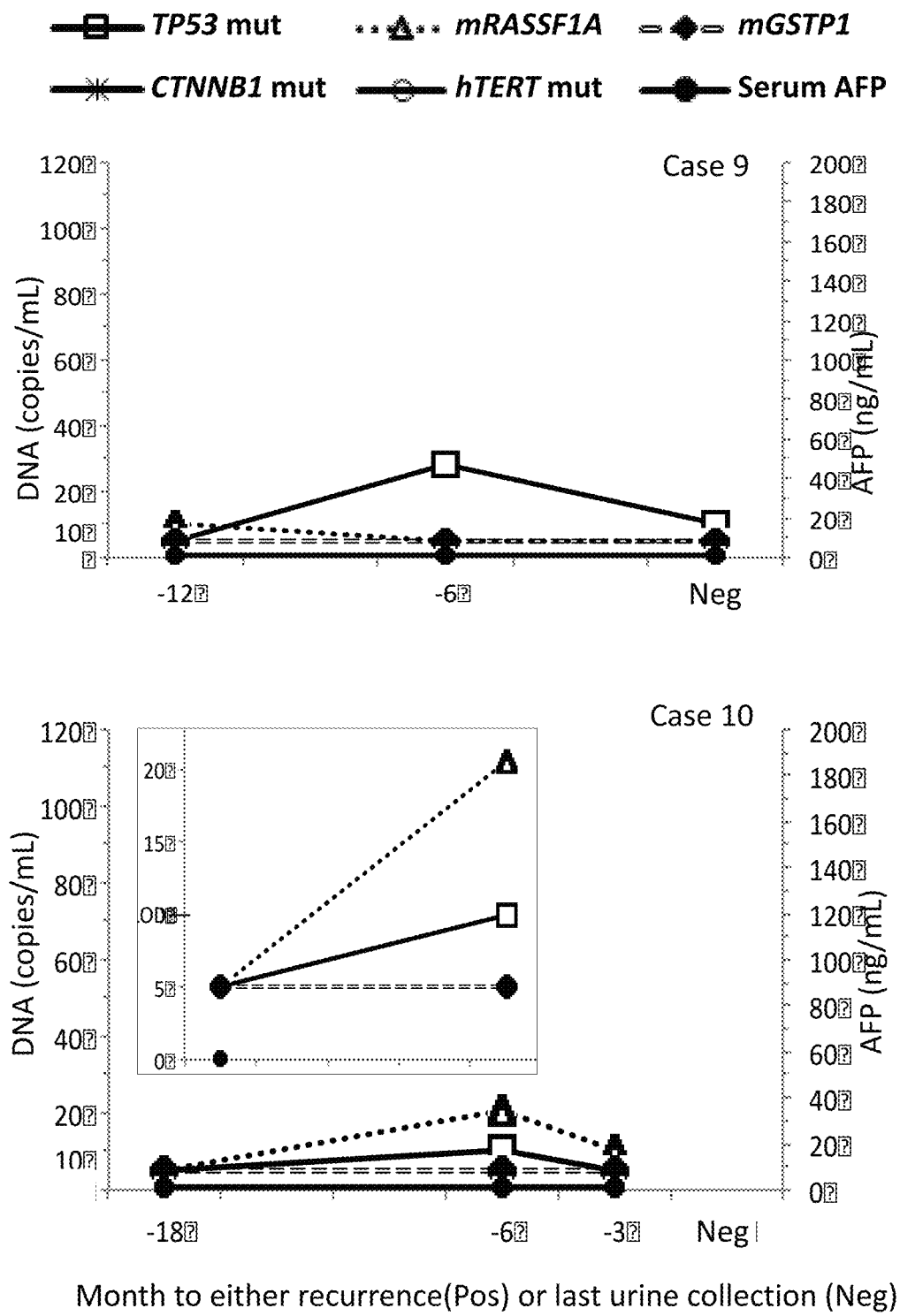

FIG. 8 shows ROC curves for serum AFP, urine DNA marker panel, and urine DNA marker panel plus serum AFP plotted to distinguish HCC (n=84) from non-HCC (97 hepatitis and 106 cirrhosis) subjects. The area under the ROC curve is shown in parenthesis. The vertical line crosses the X-axis at 90% specificity. The sensitivity of each test is listed for indicated specificities in the inserted table. Whereas AFP alone can detect 63.1% of HCC at specificity of 90% in this study cohort (n=287), the urine DNA marker panel (termed, and shown in FIG. 8, as "urine DNA markers", including the following five DNA markers: mRASSF1A, mGSTP1, and TP53, hTERT, and CTNNB1) can detect 84.5% of HCC at specificity of 90%, and the urine DNA marker panel with AFP (termed, and shown in FIG. 8, as "urine DNA markers plus AFP" in FIG. 8) can detect 89.3% of HCC at specificity of 90%.

Embodiment 4: Detection of Urine DNA Markers for Monitoring Recurrent Hepatocellular Carcinoma In this study, we demonstrate the examples of early detection of recurrent HCC by detecting five known HCC associated DNA modifications: TP53, CTNNB1, and hTERT mutation, and mGSTP1 and mRASSF1A markers in urine as compared to the MRI imaging in a small (n=10) blinded prospective study. In this study, 10 HCC patients were studied at the Liver Disease Prevention Center, Division of Gastroenterology and Hepatology, Thomas Jefferson University Hospital, Philadelphia. After curative tumor ablation, patients were monitored for recurrence by MRI and serum AFP. Urine specimens were prospectively obtained when available. The urine was retrospectively examined for the presence of the five HCC DNA biomarkers.

Urine collection, storage, and DNA isolation were carried out with written informed consent from patients as described previously in example 1. DNA from urine specimens was isolated and fractionated to obtain low molecular weight (LMW) urine DNA (<1 kb size). Bisulfite (BS) treatment of DNA was performed using the EZ DNA Methylation-Lightning™ Kit (Zymo Research, Irvine, Calif.) following manufacturer's guidelines. Five DNA modifications, TP53, CTNNB1, and hTERT mutations, aberrant promoter methylation of GSTP1 (mGSTP1), and aberrant promoter methylation of RASSF1A (mRASSF1A), were quantified in duplicate using assays kits, TP53 qPCR kit, CTNNB1 mutation qPCR kit, hTERT mutation qPCR kit, mGSTP1 qPCR kit, and mRASSF1A qPCR kit (JBS Science Inc., Doylestown, Pa.), as described previously.

FIG. 9A-9E show DNA biomarkers levels in serial urine samples from 10 patients. All patients were monitored for HCC recurrence by MRI and serum AFP. The urine samples were collected prospectively from HCC patients (when available) after curative treatment (indicated by arrows) and at follow-up visits. Samples were retrospectively measured for HCC DNA biomarkers in a blinded fashion, with a follow-up MRI diagnosis of whether or not recurrence was detected. Five DNA biomarker values (copies per ml urine), TP53, CTNNB1, and hTERT mutations, methylated RASSF1A (mRASSF1A) and methylated GSTP1 (mGSTP1), along with serum AFP (ng/mL serum), were plotted at office visits until the last available visit in which an MRI was performed. The "Pos" represents detection of HCC recurrence by MRI and the "Neg" represents no recurrence was detected by MRI at the time of the visit.

Specifically, in order to compare the detection of urine DNA markers to the currently available diagnostic methods (serum AFP and MRI imaging) for the diagnosis of HCC recurrence, urine DNA marker values were measured in a blinded fashion and plotted alongside serum AFP at the time of each collection (as shown in each panel in FIGS. 9A-9E). Briefly, urine samples were collected prospectively from HCC patients (when available) after curative treatment at follow-up visits. The samples were retrospectively analyzed for the HCC DNA biomarkers.

Of the 10 patients with >6 months of monitoring with urine DNA markers, case #1-5 had recurrence of HCC confirmed by MRI. Recurrent patients had one or more of the five DNA markers examined found in urine before or at the time of MRI diagnosis. One recurrent case (#5) died of progressive HCC. Case #6 was lost for follow up during the period of the study. Four patients (case #7-10) had no recurrence confirmed by MRI. Their urine DNA markers were either not detected (case #7), fluctuated (case #8), or detected at low levels (case #9 and #10).

Case #1

A 68 year-old male underwent transarterial chemoembolization (TACE) for HCC. Six years later, he showed tumor recurrence (Pos) by MRI. Urine specimens were obtained at 6 and 3 months prior to the MRI confirmation of recurrence (indicated as −6, −3 on the X-axis, upper panel in FIG. 9A). In the urine specimens, TP53 mutation and mRASSF1A markers were detected at 6 months prior and increased at 3 months before MRI detection of recurrence. Unfortunately urine is missing at the time of MRI imaging. His serum AFP levels remained at 2 ng/ml throughout the study, indicating the tumor was AFP-negative. (Bruix and Sherman 2005) He later received liver transplant.

Case #2

A 73 year-old male underwent TACE for HCC. Urine samples were collected after the treatment and during the follow-up period of 12 months when the tumor recurred (see lower panel in FIG. 9A). Three months after the initial TACE treatment (indicated by a black arrow on the X-axis), TP53 mutation and mRASSF1A levels were elevated while serum AFP had returned to a baseline level of 5.3 ng/ml from 88.9 ng/ml at the time of TACE treatment. These two urine DNA markers dropped to baseline on the next visit 3 months later. The TP53 mutation and serum AFP levels rose again about 3 months prior to the detection of recurrence by MRI. At the time of detection of the second recurrence (marked "Pos"), both TP53 mutation and mRASSF1A levels were elevated. Serum AFP level was at 36.4 ng/ml, indicating a rise from the baseline. Two months after the second treatment, serum AFP, TP53 mutation, and mRASSF1A all decreased. The patient did not return after this visit.

Case #3

A 55 year-old male with a 4 cm HCC received TACE. The tumor recurred 5 years later, which was treated with microwave ablation (indicated by the black arrow on the X-axis; upper panel in FIG. 9B). The tumor recurred again during a follow up appointment 3 months later (marked "Pos"; upper panel in FIG. 9B). Urine DNA markers at two visits prior to the first recurrence were below the level of detection. However, mGSTP1 was elevated one month after microwave treatment. Interestingly, when the tumor recurred for a second time (1.6 cm) 3 months after treatment, the mGSTP1 was undetectable while TP53 mutation was elevated. This may indicate the heterogeneity of HCC. Note, the serum AFP levels were below 20 ng/mL in the period of study.

Case #4

A 54 year-old male diagnosed with HCC and elevated AFP. Urine was collected at the time of diagnosis and treatment with microwave ablation (lower panel in FIG. 9B). The DNA marker mGSTP1 was highly elevated in urine at the time of HCC diagnosis. Two months after treatment, both urine mGSTP1 and serum AFP levels decreased to the normal range while urine mRASSF1A was elevated. This could be due to the apoptotic tumor cells following microwave treatment. At the next visit three months later, mRASSF1A decreased but remained detectable while the two other DNA markers, TP53 mutation and mGSTP1, increased. Four months later, an MRI detected a recurrent tumor (solid lesion). Unfortunately, the urine was not collected at "–2" and at the time of diagnosis "Pos", hence there is no marker data available at these time points.

Case #5

A 56 year-old male underwent TACE for HCC. Urine was collected on the day of treatment and at a follow-up visit 1 month later (upper panel in FIG. 9C). The mRASSF1A marker was detected in the urine on the day of TACE treatment, and the levels of mRASSF1A and hTERT mutation was detected in the urine on the day of TACE treatment, and the levels of mRASSF1A and hTERT mutation dropped one month following treatment. Similarly, serum AFP levels decreased nearly 10-fold from 3770 ng/ml to 323 ng/ml. However, four months later MRI detected HCC recurrence and increased levels of serum AFP (1522 ng/ml). The patient continued to have active HCC with detectable CTNNB1 mutation and mRASSF1A. Despite receiving another TACE treatment, the patient passed away 8 months later.

Case #6

A 56 year-old male with HCC underwent TACE. Urine samples were collected at 3 and 4 years after TACE. mRASSF1A was found elevated at 3 years and negative at 4 years post TACE. The patient has had no recurrence (lower panel in FIG. 9C). AFP was in normal range. The patient was lost for follow up.

Case #7

A 58 year-old male with HCC received TACE followed by radiofrequency ablation (RFA). Urine collection started one year after RFA. No biomarkers were detected 2 years post RFA, as the patient remained recurrence free (upper panel in FIG. 9D).

Case #8

A 62 year-old male with HCC received RFA. Urine samples were collected on the day of treatment and every three months after for 9 months (lower panel in FIG. 9D). Serum AFP, TP53 mutation, and mRASSF1A levels were all elevated on the day of RFA, and decreased 3 and 6 months following the treatment to below the limit of detection. There has been no recurrence by MRI.

Case #9

A 27 year-old female was diagnosed with HCC at age 20 and the original tumor was treated three times with TACE in a three-year period. Urine was collected every six months starting 4 years after the last TACE. TP53 mutation was detected in the urine collected on the second visit and decreased, but remained detectable in the third urine sample as indicated in upper panel in FIG. 9E. MRI suggested a mass in the liver, but the mass was not confirmed as recurrent HCC. The serum AFP levels were below 20 ng/mL in the period of study. The patient has been on antiviral treatment since the diagnosis of HCC.

Case #10

A 66 year-old male with HCC underwent RFA followed by resection. He has had no recurrence for the past 10 years. Two urine samples were collected at 8 years (–18) and 9 years (–6) after resection (lower panel in FIG. 10E). Serum AFP is normal, and none of the DNA markers were detected until 6 months prior to the MRI, when the TP53 mutation and mRASSF1A markers were elevated (lower panel in FIG. 9E). TP53 mutation reverted to baseline and mRASSF1A levels declined three months later (–3). At the time of MRI testing there was no HCC recurrence detected from the visit.

This study demonstrates the applicability of using urine DNA markers in combination with serum AFP for the early detection of HCC recurrence in a small 10-case study. HCC recurrence is known to be the major factor for poor prognosis. In this small 10-case study, MRI identified recurrence in 5 out of 10 patients (cases 1-5). Encouragingly, for all four recurrent patients that remain in the study (cases 1-4), urine DNA markers were found to be elevated in urine samples as early as 9 months before MRI confirmation.

Although this is a small longitudinal 10 patient study, the use of these urine DNA markers for management of HCC recurrence and important characteristics of HCC recurrence is demonstrated. First, for all remaining recurrent cases (case #1-4), DNA markers were elevated before or at the time of diagnosis by MRI imaging. MRI/CT imaging is the gold standard for diagnosis of recurrent HCC, but has difficulty in detecting early recurrence in the previously treated areas (especially after local ablation). This may explain why the DNA markers were found in urine earlier than MRI diagnosis. Secondly, HCC, like other cancers, is a disease of the genome. Detection of genetic drivers of HCC may provide not only sensitive and earlier detection for monitoring HCC recurrence, but may also provide HCC genetic information to assist in patient management. Furthermore, since collection of urine can potentially be done at home and then shipped to certified laboratories for testing, the urine screening may result in better compliance while not requiring a doctor's office visit. Lastly, the levels of DNA biomarkers in urine can also be useful to measure effectiveness of cancer treatments that induces apoptosis of tumor cells. We have shown that circulating tumor DNA found in urine was mostly from apoptotic tumor cells. The treatment that induce apoptosis should increase the amount of tumor derived DNA deposited in the blood and secreted into urine. This could be the circumstance for cases #2, #3, #4 and #5 where an elevated mRASSF1A, mGSTP1, CTNNB1 mutation, and hTERT mutation markers were detected after the treatment, suggesting the potential to use urine DNA markers to monitor effectiveness of therapy that induces tumor cell apoptosis.

Finally, HCC is often recognized as being multi-clonal. Interestingly, in recurrent case #3, mGSTP1 levels returned to not detectable in urine while TP53 mutation was elevated in the urine collected 3 month later with the MRI report of a 1.6 cm lesion. We speculate that the rising of the TP53 mutated clone was different from the previously treated tumor nodule and was either not responding to the treatment or was derived from tumor evolution.

It is important to note that the levels of urine DNA markers can fluctuate for several reasons including hydration of the patient at time of collection (which can result in diluted DNA in the urine). Therefore the use of an internal control is important for appropriately setting cutoffs for the urine marker values.

In conclusion, we have demonstrated that urine DNA biomarker testing can be used for the early detection of HCC recurrence, can overcome the inherent limitations of imaging technology, thus to provide a highly sensitive tool for monitoring HCC recurrence.

REFERENCES

American Cancer Society (2017). "Cancer Facts and Figures" Anker, P., J. Lyautey, C. Lederrey and M. Stroun (2001). "Circulating nucleic acids in plasma or serum." *Clinica Chimica Acta* 313: 143-146.

Bruix, J. and M. Sherman (2005). "Management of hepatocellular carcinoma." *Hepatology* 42(5): 1208-1236.

Bruix, J. and M. Sherman (2011). "Management of hepatocellular carcinoma: An update." *Hepatology* 53(3): 1020-1022.

Chan, A. K. C., R. W. K. Chiu and Y. M. D. Lo (2003). "Cell-free nucleic acids in plasma, serum and urine: a new tool in molecular diagnosis." *Annals of clinical biochemistry* 40(2): 122-130.

Diehl, F., K. Schmidt, M. A. Choti, K. Romans, S. Goodman, M. Li, K. Thornton, N. Agrawal, L. Sokoll, S. A. Szabo, K. W. Kinzler, B. Vogelstein and L. A. Diaz Jr (2008). "Circulating mutant DNA to assess tumor dynamics." *Nat Med* 14(9): 985-990.

Gerszten, R. E. and T. J. Wang (2008). The search for new cardiovascular biomarkers. *Nature.* 45: 949-952.

Harder, J., O. G. Opitz, J. Brabender, M. Olschewski, H. E. Blum, S. Nomoto and H. Usadel (2008). "Quantitative promoter methylation analysis of hepatocellular carcinoma, cirrhotic and normal liver." *International Journal of Cancer* 122(12): 2800-2804.

Howlader N, N. A., Krapcho M, Miller D, Bishop K, Altekruse S F, Kosary C L, Yu M, Ruhl J, Tatalovich Z, Mariotto A, Lewis D R, Chen H S, Feuer E J, Cronin K A (eds) (2016). "SEER Cancer Statistics Review, 1975-2013, National Cancer Institute. Bethesda, Md., http://seer.cancer.gov/csr/1975_2013/, based on November 2015 SEER data submission, posted to the SEER web site, April 2016.".

Hung, I. F.-N., D. K.-H. Wong, R. T.-P. Poon, D. Y.-T. Fong, A. H.-W. Chui, W.-K. Seto, J. Y.-Y. Fung, A. C.-Y. Chan, J. C.-H. Yuen, R. Tiu, O. Choi, C.-L. Lai and M.-F. Yuen (2016). "Risk Factors and Post-Resection Independent Predictive Score for the Recurrence of Hepatitis B-Related Hepatocellular Carcinoma." *PLoS ONE* 11(2): e0148493.

Kamiyama, T., K. Nakanishi, H. Yokoo, H. Kamachi, M. Tahara, T. Suzuki, T. Shimamura, H. Furukawa, M. Matsushita and S. Todo (2009). "Recurrence Patterns After Hepatectomy of Hepatocellular Carcinoma: Implication of Milan Criteria Utilization." *Annals of Surgical Oncology* 16(6): 1560-1571.

Lin, S. Y., V. Dhillon, S. Jain, T. T. Chang, C. T. Hu, Y. J. Lin, S. H. Chen, K. C. Chang, W. Song, L. Yu, T. M. Block and Y. H. Su (2011). "A locked nucleic acid clamp-mediated PCR assay for detection of a p53 codon 249 hotspot mutation in urine." *J Mol Diagn* 13 (5): 474-484.

Minami, Y. and M. Kudo (2015). "Imaging Modalities for Assessment of Treatment Response to Nonsurgical Hepatocellular Carcinoma Therapy: Contrast-Enhanced US, CT, and MRI." *Liver Cancer* 4(2): 106-114.

Minami, Y., N. Nishida and M. Kudo (2014). "Therapeutic response assessment of RFA for HCC: Contrast-enhanced US, CT and MRI." *World Journal of Gastroenterology: WJG* 20(15): 4160-4166.

Nault, J. C., M. Mallet, C. Pilati, J. Calderaro, P. Bioulac-Sage, C. Laurent, A. Laurent, D. Cherqui, C. Balabaud and J. Zucman-Rossi (2013). "High frequency of telomerase reverse-transcriptase promoter somatic mutations in hepatocellular carcinoma and preneoplastic lesions." *Nat Commun* 4.

Newell, P., S. Toffanin, A. Villanueva, D. Y. Chiang, B. Minguez, L. Cabellos, R. Savic, Y. Hoshida, K. H. Lim, P. Melgar-Lesmes, S. Yea, J. Peix, K. Deniz, M. I. Fiel, S. Thung, C. Alsinet, V. Tovar, V. Mazzaferro, J. Bruix, S. Roayaie, M. Schwartz, S. L. Friedman and J. M. Llovet (2009). "Ras pathway activation in hepatocellular carcinoma and anti-tumoral effect of combined sorafenib and rapamycin in vivo." *Journal of Hepatology* 51(4): 725-733.

Nishida, N., T. Nagasaka, T. Nishimura, I. Ikai, C. R. Boland and A. Goel (2008). "Aberrant methylation of multiple tumor suppressor genes in aging liver, chronic hepatitis, and hepatocellular carcinoma." *Hepatology* 47: 908-918.

Nomoto, S., T. Kinoshita and K. Kato (2007). "Hypermethylation of multiple genes as clonal markers in multicentric hepatocellular carcinoma." *Br J Cancer* 97(9): 1260, 1265.

Pepe, M. S. and M. L. Thompson (2000). "Combining diagnostic test results to increase accuracy." *Biostatistics* 1: 123-140.

Sherman, M. (2008). "Recurrence of Hepatocellular Carcinoma." *New England Journal of Medicine* 359(19): 2045-2047.

Simard, E. P., E. M. Ward, R. Siegel and A. Jemal (2012). "Cancers with increasing incidence trends in the United States: 1999 through 2008." *CA: A Cancer Journal for Clinicians* 62(2): 118-128.

Song, B. P., S. Jain, S. Y. Lin, Q. Chen, T. M. Block, W. Song, D. E. Brenner and Y. H. Su (2012). "Detection of hypermethylated vimentin in urine of patients with colorectal cancer." *J Mol Diagn* 14(2): 112-119.

Su, Y. H., J. Song, Z. Wang, X. H. Wang, M. Wang, D. E. Brenner and T. M. Block (2008). "Removal of High-Molecular-Weight DNA by Carboxylated Magnetic Beads Enhances the Detection of Mutated K-ras DNA in Urine." *Annals of the New York Academy of Sciences* 1137(1): 82-91.

Su, Y. H., M. Wang, B. Aiamkitsumrit, D. E. Brenner and T. M. Block (2005). "Detection of a K-ras mutation in urine of patients with colorectal cancer." *Cancer Biomark* 1(2-3): 177-182.

Su, Y. H., M. Wang, D. E. Brenner, A. Ng, H. Melkonyan, S. Umansky, S. Syngal and T. M. Block (2004). "Human urine contains small, 150 to 250 nucleotide-sized, soluble DNA derived from the circulation and may be useful in the detection of colorectal cancer." *Journal of Molecular Diagnostics* 6(2): 101-107.

Su, Y. H., M. Wang, D. E. Brenner, P. A. Norton and T. M. Block (2008). "Detection of mutated K-ras DNA in urine, plasma, and serum of patients with colorectal carcinoma or adenomatous polyps." *Ann NY Acad Sci* 1137: 197-206.

Willatt, J. M., H. K. Hussain, S. Adusumilli and J. A. Marrero (2008). "MR Imaging of Hepatocellular Carcinoma in the Cirrhotic Liver: Challenges and Controversies." *Radiology* 247(2): 311-330.

Yang, B., M. Guo, J. G. Herman and D. P. Clark (2003). "Aberrant Promoter Methylation Profiles of Tumor Suppressor Genes in Hepatocellular Carcinoma." *American Journal of Pathology* 163 (3): 1101-1107.

Zhang, Z., Y. Yu, F. Xu, A. Berchuck, C. van Haaften-Day, L. J. Havrilesky, H. W. A. de Bruijn, A. G. J. van der Zee, R. P. Woolas, I. J. Jacobs, S. Skates, D. W. Chan and R. C. Bast Jr (2007). "Combining multiple serum tumor markers improves detection of stage I epithelial ovarian cancer." *Gynecologic Oncology* 107(3): 526-531.

The invention claimed is:

1. A kit for characterizing, in a biological sample containing at least one first allele of a gene, at least one second allele in a genomic region of the gene, the kit comprising:
   a first pair of primers, configured to specifically bind sequences flanking the genomic region to thereby allow amplification of at least one polynucleotide harboring the genomic region in a first PCR reaction; and
   at least one clamp, each configured to bind to one of the at least one first allele but not any of the at least one second allele at an annealing temperature in the first PCR reaction to thereby selectively suppress amplification of the one of the at least one first allele but still allow amplification of the at least one second allele:
   wherein:
      the gene is hTERT, the genomic region comprises nucleotide position −129 to −119 upstream from a start codon of hTERT, the at least one first allele comprises a wildtype allele of hTERT, the at least one second allele comprises one or more mutant alleles of hTERT in the genomic region, and the at least one clamp comprises a bridged nucleic acid (BNA) clamp specifically targeting the wildtype allele of hTERT;
      at least one of the first pair of primers comprises an oligonucleotide of an artificial sequence at a 5'-end thereof, configured to interrupt a secondary structure of DNA molecules of the gene or to increase a Tm of the at least one of the first pair of primers in the first PCR reaction using amplified products as templates to thereby increase an efficiency of the amplification of the at least one polynucleotide in the first PCR reaction; and
      the first pair of primers respectively have nucleotide sequences comprising SEQ ID NO: 11 and SEQ ID NO: 12.

2. A kit for characterizing, in a biological sample containing at least one first allele of a gene, at least one second allele in a genomic region of the gene, the kit comprising:
   a first pair of primers, configured to specifically bind sequences flanking the genomic region to thereby allow amplification of at least one polynucleotide harboring the genomic region in a first PCR reaction; and
   at least one clamp, each configured to bind to one of the at least one first allele but not any of the at least one second allele at an annealing temperature in the first PCR reaction to thereby selectively suppress amplification of the one of the at least one first allele but still allow amplification of the at least one second allele;
   wherein:
      the gene is hTERT, the genomic region comprises nucleotide position −129 to −119 upstream from a start codon of hTERT, the at least one first allele comprises a wildtype allele of hTERT, the at least one second allele comprises one or more mutant alleles of hTERT in the genomic region, and the at least one clamp comprises a bridged nucleic acid (BNA) clamp specifically targeting the wildtype allele of hTERT;
      at least one of the first pair of primers comprises an oligonucleotide of an artificial sequence at a 5'-end thereof, configured to interrupt a secondary structure of DNA molecules of the gene or to increase a Tm of the at least one of the first pair of primers in the first PCR reaction using amplified products as templates to thereby increase an efficiency of the amplification of the at least one polynucleotide in the first PCR reaction; and
      the kit further comprises a hydrolysis probe having a nucleotide sequence comprising SEQ ID NO: 15 or SEQ ID NO: 16, configured to respectively allow detection or quantification of the wildtype allele or any of the one or more mutant alleles of hTERT in a second PCR reaction over the at least one polynucleotide obtained from the first PCR reaction.

3. The kit of claim 2, further comprising a second pair of primers respectively having nucleotide sequences comprising SEQ ID NO: 11 and SEQ ID NO: 14, configured to be employed in the second PCR reaction.

* * * * *